United States Patent [19]

Maginot

[11] Patent Number: 5,211,683
[45] Date of Patent: May 18, 1993

[54] METHOD OF IMPLANTING A GRAFT PROSTHESIS IN THE BODY OF A PATIENT

[76] Inventor: Thomas J. Maginot, 2811 Princeton Ave., St. Louis Park, Minn. 55416

[21] Appl. No.: 725,597

[22] Filed: Jul. 3, 1991

[51] Int. Cl.$^5$ ............................................. A61B 19/00
[52] U.S. Cl. ........................................ 128/898; 623/1; 606/159
[58] Field of Search ........................ 606/153, 155, 159; 623/1, 12; 600/29, 30; 128/898

[56] References Cited

U.S. PATENT DOCUMENTS

| | | |
|---|---|---|
| 3,710,777 | 1/1973 | Sparks . |
| 3,866,247 | 2/1975 | Sparks . |
| 4,061,134 | 12/1977 | Samuels et al. . |
| 4,183,102 | 1/1980 | Guiset . |
| 4,190,909 | 3/1980 | Ablaza . |
| 4,441,215 | 4/1984 | Kaster . |
| 4,503,568 | 3/1985 | Madras . |
| 4,503,569 | 3/1985 | Dotter . |
| 4,546,499 | 10/1985 | Possis et al. . |
| 4,562,597 | 1/1986 | Possis et al. . |
| 4,617,932 | 10/1986 | Kornberg . |
| 4,655,771 | 4/1987 | Wallsten . |
| 4,743,251 | 5/1988 | Barra . |
| 4,769,029 | 9/1988 | Patel ................................. 606/155 |
| 4,776,337 | 10/1988 | Palmaz . |
| 4,787,899 | 11/1988 | Lazarus . |
| 4,795,458 | 1/1989 | Regan . |
| 4,830,003 | 5/1989 | Wolff et al. . |
| 4,856,516 | 8/1989 | Hillstead . |
| 4,872,874 | 10/1989 | Taheri . |
| 4,890,612 | 1/1990 | Kensey . |
| 4,892,539 | 1/1990 | Koch . |
| 4,929,246 | 5/1990 | Sinofsky . |
| 4,938,740 | 7/1990 | Melbin . |
| 4,954,126 | 9/1990 | Wallsten . |
| 4,957,508 | 9/1990 | Kaneko et al. . |
| 5,078,726 | 1/1992 | Kreamer . |
| 5,078,735 | 1/1992 | Mobin-Uddin ........................ 623/1 |

OTHER PUBLICATIONS

Salky and Berci, Laparoscopy For Surgeons, copyright 1990, p. 6.
Gallstones: Laparoscopic Treatment, Intracorporeal Lithotripsy Followed by Cholecystostomy or Cholecystectomy-A Personal Technique; Endoscopy, 1989; 21:373-374; Authored by J. Perissat et al.
Laparoscopic Laser Cholecystectomy; Laser Medicine and Surgery News and Advances, 1989; (7)1:38-40; Authored by Eddie J. Reddick et al.
Coelioscopic cholecystectomy; Annals of Surgery, Jan. 1990; 211(1):60-62; Authored by F. Dubois et al.

(List continued on next page.)

Primary Examiner—Randall L. Green
Assistant Examiner—Gina M. Gualtieri
Attorney, Agent, or Firm—Paul J. Maginot

[57] ABSTRACT

A method of implanting a graft prosthesis in the body of a patient to bypass a segment of a blood vessel. A graft is positioned so that one end of the graft is located substantially adjacent the blood vessel at a site upstream of the segment and the other end of the graft is located substantially adjacent the blood vessel at a site downstream of the segment, wherein the positioning step includes the step of advancing the graft within the body with a medical instrument. A region of the area within the blood vessel near the upstream site is isolated from fluid communication with the rest of the area within the blood vessel. An arteriotomy is made in the sidewall of the blood vessel near the upstream site to create a communicating aperture between the upstream isolated region and the outside of the blood vessel. An anastomosis is then formed between the one end of the graft and the blood vessel near the upstream site. Moreover, a region of the area within the blood vessel near the downstream site is isolated from fluid communication with the rest of the area within the blood vessel. An arteriotomy is made in the sidewall of the blood vessel near the downstream site to create a communicating aperture between the downstream isolated region and the outside of the blood vessel. An anastomosis is then formed between the other end of the graft and the blood vessel near the downstream site.

40 Claims, 23 Drawing Sheets

OTHER PUBLICATIONS

*Color Atlas of Vascular Surgery;* Published by Wolfe Medical Publications Ltd. of Baltimore, Md. (1986); printed by W. S. Cowell, Ltd. of Ipswich, United Kingdom; Authored by John S. P. Lumley; pp. 9-42 and 172-185.

*Experimental Intrahepatic Portacaval Anastomosis: Use of Expandable Giantturco Stents;* Radiology, 1987; 162:481-485; Authored by J. Rosch et al.

*Intravascular Stents to Prevent Occlusion and Restenosis After Transluminal Angioplasty;* New England Journal of Medicine, 1987; 316:701-716; Authored by U. Sigwart et al.

*Percutaneously Placed Endovascular Grafts for Aortic Aneurysms: Feasibility Study;* Radiology, 1989; 170:1033-1037; Authored by D. Mirich et al.

*Vascular Surgery;* W. B. Saunders Company, Harcourt Brace Jovanovich, Inc. (Phila.)(1989); Authored by Robert B. Rutherford; pp. 404-408, 450-460 and 667-691.

*Long-term Results of Aortoiliac Reconstruction;* Journal of Vascular and Interventional Radiology, Nov. 1990; 1:49-55; Authored by T. E. Brothers et al.

*Placement of Balloon-expandable Intraluminal Stents in Iliac Arteries: First 171 Procedures;* Radiology, 1990; 174:969-975; Authored by J. C. Palmaz et al.

*Laparoscopy for surgeons;* Published by Igaku-Shoin Medical Publishers, Inc. of New York, N.Y., U.S.A. (1990); Authored by Barry A. Sulky; pp. 1-16 and 136-143.

*Refinements Widen Utility of Interventional Devices;* Diagnostic Imaging, May 1991; 100-107; Authored by B. T. Katzen.

*Stents Aid PTA in Battle to Reduce Restenosis Rates;* Diagnostic Imaging, Jul. 1991; 106-113; Authored by L. D'Agincourt.

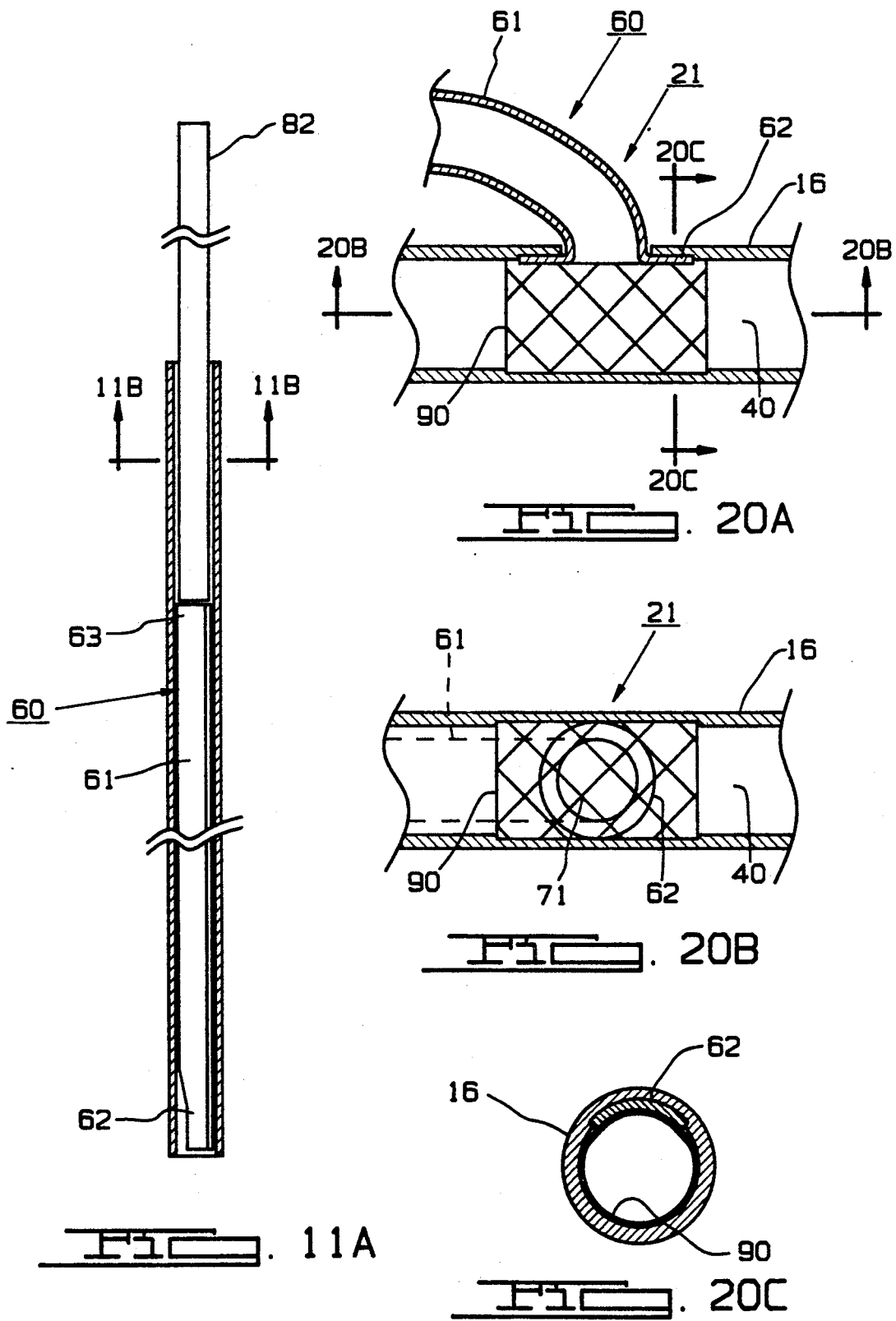

METHOD OF IMPLANTING A GRAFT PROSTHESIS IN THE BODY OF A PATIENT

BACKGROUND OF THE INVENTION

The present invention relates generally to a method of improving blood flow in the body of a patient and more particularly concerns a method of implanting a graft prosthesis to bypass a segment of a blood vessel.

Treatment of vascular disease in which the lumen of a blood vessel is significantly narrowed or occluded by atherosclerosis includes surgical and endovascular methods. Conventional surgical methods include obtaining access to a blood vessel via one or more surgical incisions and either removing the blockage by performing an endarterectomy or bypassing the blockage by placing a bypass graft. Endovascular methods include obtaining access to a blood vessel with a catheter and improving blood flow therein by performing an athrectomy, atherolysis, or balloon and laser angioplasty with or without endovascular stent placement. In general, the preferred treatment of severe stenosis or occlusion of a long vessel segment has been surgical bypass grafting.

Although conventional surgical bypass grafting is an accepted procedure, it presents substantial morbidity and mortality risks. Also, not all patients are acceptable candidates for the above surgical procedure due to advanced age and preexisting medical conditions. Moreover, conventional surgical bypass grafting is an invasive procedure which may require extended hospitalization due to postoperative recovery. In addition, the above surgical procedure may involve substantial financial costs to patients, hospitals and society in general. Further, incisions made during the above surgical procedure may cause significant cosmetically unattractive scarring which is undesirable to many patients.

SUMMARY OF THE INVENTION

One embodiment of the present invention involves a method of implanting a graft prosthesis in the body of a patient to bypass an occluded segment of a blood vessel. A graft is positioned so that one end of the graft is located substantially adjacent the blood vessel at a site upstream of the occluded segment and another end of the graft is located substantially adjacent the blood vessel at a site downstream of the occluded segment, wherein the positioning step includes the step of advancing the graft within the body with a medical instrument. A region of the area within the blood vessel near the upstream site is isolated from fluid communication with the rest of the area within the blood vessel. An arteriotomy is made in the sidewall of the blood vessel near the upstream site to create a communicating aperture between the upstream isolated region and the outside of the blood vessel. An anastomosis is then formed between the one end of the graft and the blood vessel near the upstream site. Moreover, a region of the area within the blood vessel near the downstream site is isolated from fluid communication with the rest of the area within the blood vessel. An arteriotomy is made in the sidewall of the blood vessel near the downstream site to create a communicating aperture between the downstream isolated region and the outside of the blood vessel. An anastomosis is then formed between the other end of the graft and the blood vessel near the downstream site.

Another embodiment of the present invention involves a method for implanting an end portion of a graft within the body of a patient. An incision is made in the body at a first location. The end portion of the graft is advanced through the incision to a second location, wherein the advancing step includes the step of advancing the end portion of the graft within the body with a medical instrument. The end portion of the graft is then secured to a blood vessel of the body near the second location.

One object of the present invention is to provide an improved method for implanting a graft prosthesis in the body of a patient.

Another object of the present invention is to provide an improved method for implanting an end portion of a graft within the body of a patient.

Still another object of the present invention is to provide a method of implanting a graft prosthesis in the body of a patient which is less invasive relative to conventional surgical bypass grafting procedures.

Yet another object of the present invention is to provide a method of implanting a graft prosthesis in the body of a patient which obviates at least one surgical incision (e.g. the abdominal surgical incision) as compared to conventional surgical bypass grafting procedures.

Still another object of the present invention is to provide a method of implanting a graft prosthesis in the body of a patient which has low morbidity and mortality risk to patients.

Yet another object of the present invention is to provide a method of implanting a graft prosthesis in the body of a patient which can be performed on patients whom are elderly or have poor preexisting medical conditions.

Still another object of the present invention is to provide a method of implanting a graft prosthesis in the body of a patient which requires relatively less financial costs to patients, hospitals and society in general as compared to conventional surgical bypass grafting techniques.

Other objects and benefits of the present invention can be discerned from the following description and accompanying drawings.

BRIEF DESCRIPTION OF THE DRAWINGS

FIG. 1 also shows a portion of each inguinal ligament of the human body.

FIG. 11A is an elevational view of the laparoscope of FIG. 6. Moreover, FIG. 11A shows the graft prosthesis of FIG. 10A, positioned within the laparoscope in accordance with the method of the present invention. FIG. 11A further shows a plunger, used in carrying out the preferred method of the present invention, partially positioned within the laparoscope in accordance with the preferred method of the present invention.

FIG. 20A is an enlarged side elevational view showing the anastomosis of FIG. 19.

FIG. 20B is a cross-sectional view taken along the line 20B—20B of FIG. 20A as viewed in the direction of the arrows.

FIG. 20C is a cross-sectional view taken along the line 20C—20C of FIG. 20A as viewed in the direction of the arrows.

DESCRIPTION OF THE PREFERRED EMBODIMENT

Figure 1:
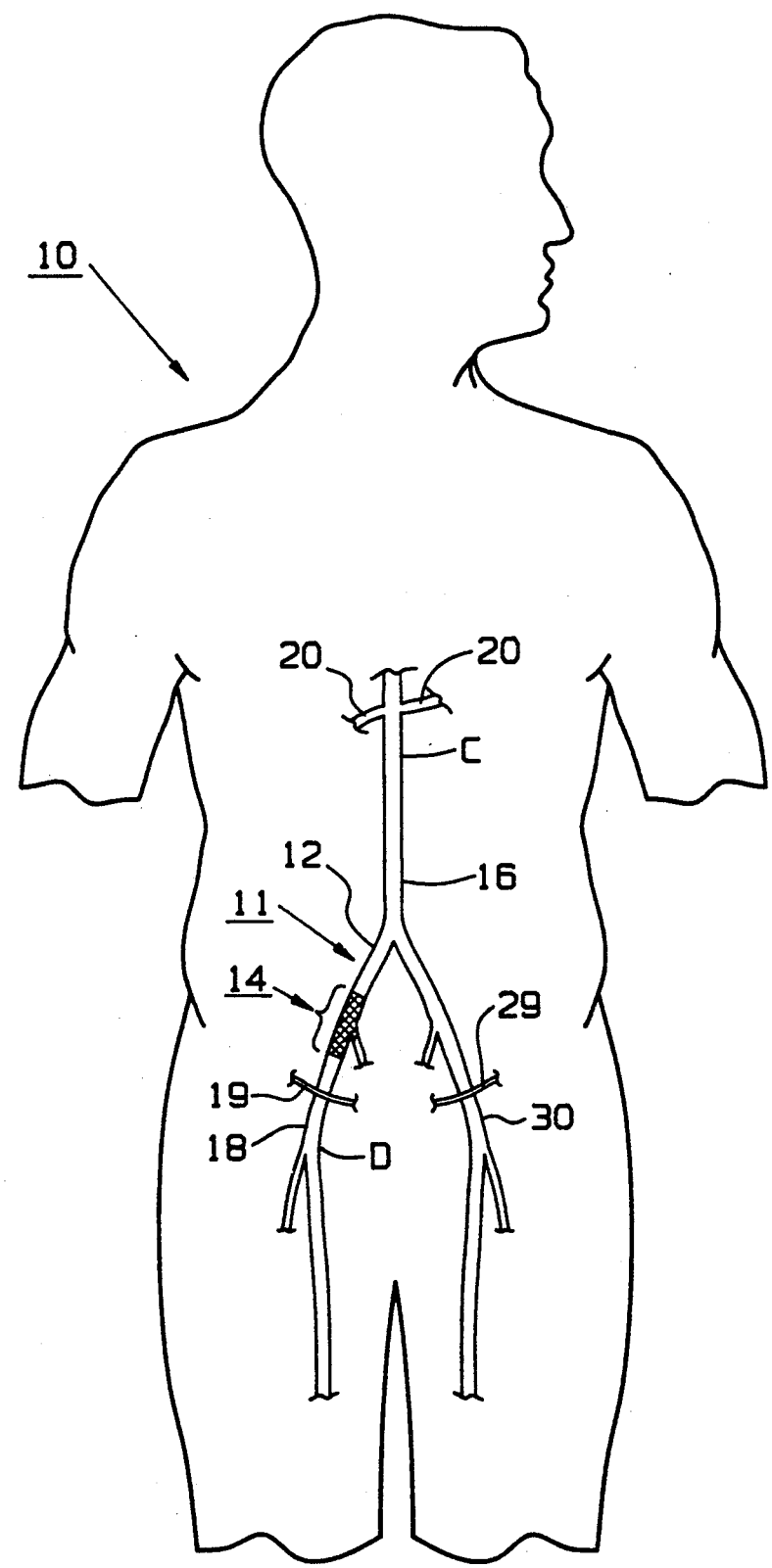
FIG. 1 is a fragmentary front elevational view of a human body showing a blood vessel which includes the aorta, the right common iliac artery, the right common femoral artery and the left common femoral artery wherein a segment of the blood vessel is occluded.

For the purposes of promoting an understanding of the principles of the invention, reference will now be made to the embodiments and methods illustrated in the drawings and specific language will be used to describe the same. It will nevertheless be understood that no limitation of the scope of the invention is thereby intended, such alterations and further modifications in the illustrated devices and methods, and such further applications of the principles of the invention as illustrated therein being contemplated as would normally occur to one skilled in the art to which the invention relates.

Figure 2:
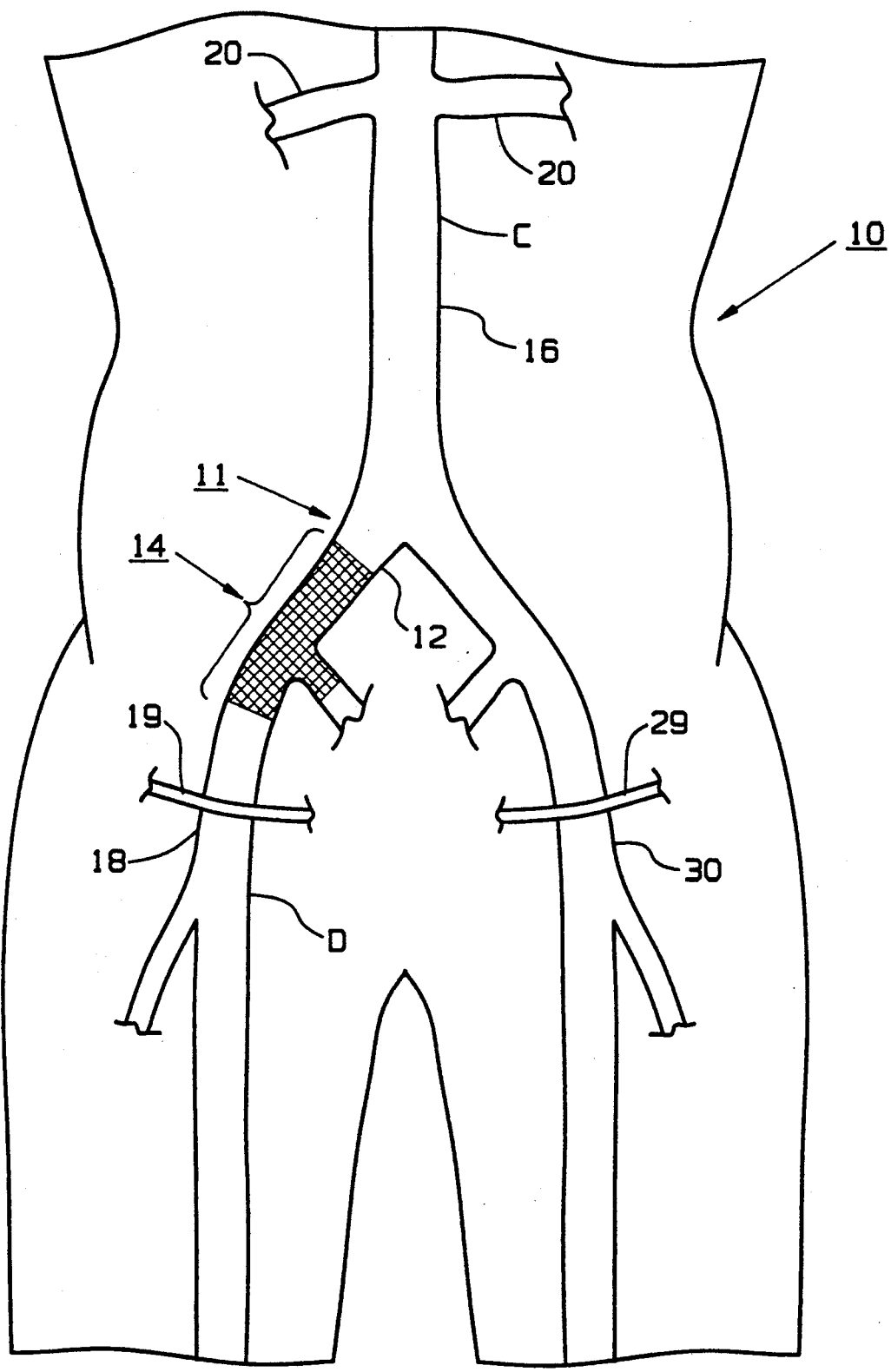
FIG. 2 is an enlarged fragmentary view of the human body and blood vessel of FIG. 1.

Referring now to the drawings, FIG. 1 shows a portion of a human body, generally designated by the reference numeral 10, with an artery, the common iliac artery 12, having an occluded segment, generally designated by the reference numeral 14. Human body 10 is further shown having other arteries, in particular, aorta 16, right common femoral artery 18, left common femoral artery 30 and renal arteries 20. In addition, human body 10 includes a right inguinal ligament 19 and a left inguinal ligament 29. Human body 10 also includes an epidermis 13 (see e.g. FIG. 6). The preferred method disclosed herein describes the implantation of a craft to couple aorta 16 to right common femoral artery 18 thereby bypassing occluded segment 14. FIG. 2 shows an enlarged view of aorta 16, right common iliac artery 12, occluded segment 14, right common femoral artery 18, left common femoral artery 30, renal arteries 20 and right inguinal ligament 19. In FIGS. 1 and 2, a blood vessel is shown, generally designated by the reference numeral 11, which includes aorta 16, right common iliac artery 12, right common femoral artery 18 and left common femoral artery 30. Blood vessel 11, when not occluded, conveys blood from a point C within aorta 16 to a point D within right common femoral artery 18 (see FIGS. 1-2). However, due to the presence of occluded segment 14, blood is substantially totally precluded from being conveyed from point C within aorta 16 to point D within right common femoral artery 18 via the direct route of right common iliac artery 12. While the inventive method will hereinafter be described with regard to a substantially totally occluded segment within a blood vessel of a patient, it will be understood to one skilled in the art that the inventive method is equally effective for bypass of a partially occluded segment of a blood vessel. In addition, the inventive method is also useful for bypass of an aneurysmal segment of a blood vessel.

Referring now to FIGS. 3-24, successive steps according to the preferred method of the present invention are depicted of the implantation of a graft prosthesis to couple aorta 16 to right common femoral artery 18 thereby bypassing occluded segment 14 of blood vessel 11.

One step of the preferred method of the present invention comprises isolating a region of the area within blood vessel 11, located near a site 21 (see FIG. 4) upstream of occluded segment 14, from fluid communication with the rest of the area within the blood vessel. There also exists a site 31 which is located downstream of occluded segment 14 (see FIG. 4).

Figure 3:
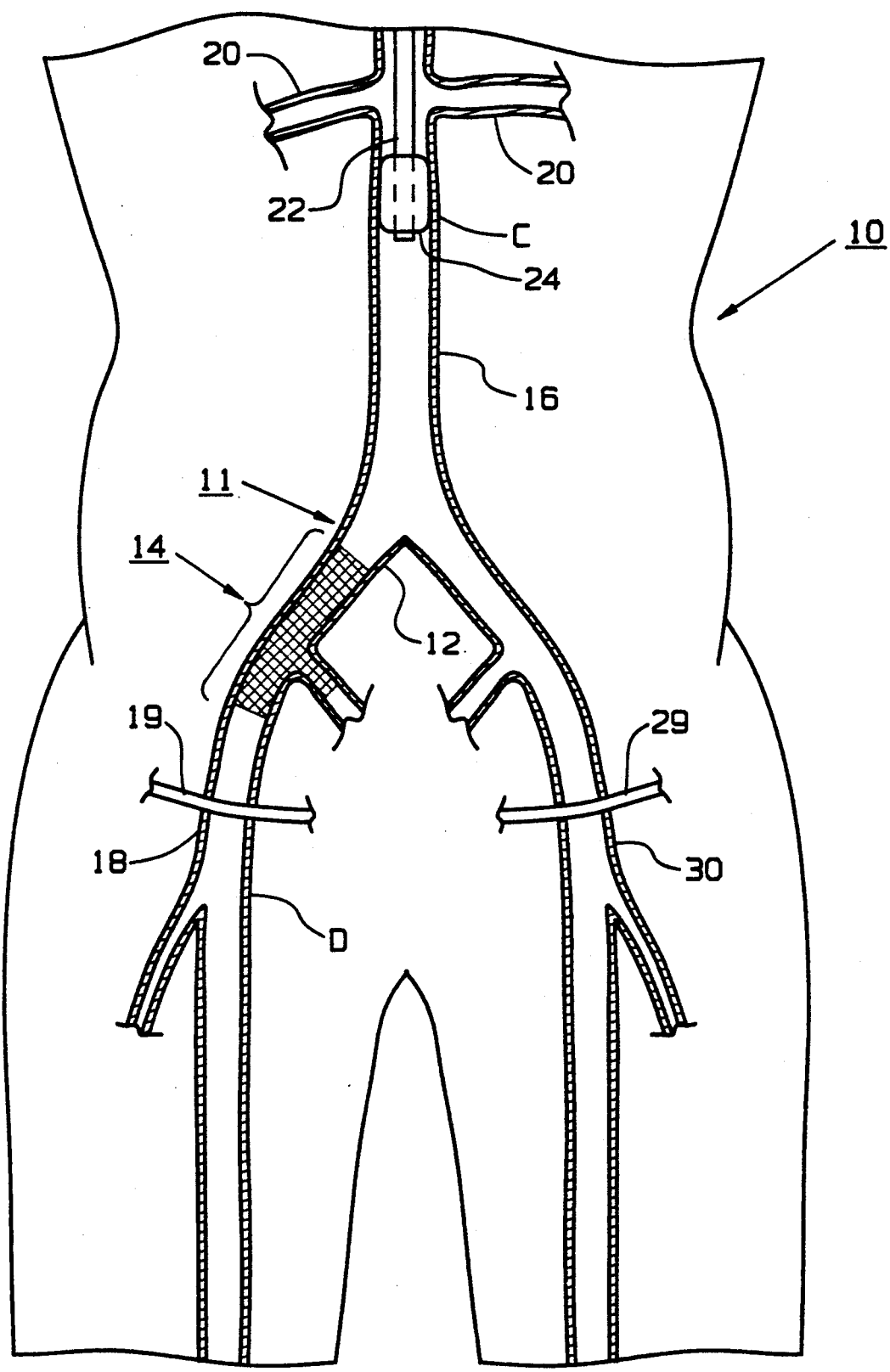
FIG. 3 shows the human body and blood vessel of FIG. 2 with a balloon-tip catheter positioned within the blood vessel wherein the balloon is inflated in accordance with the preferred method of the present invention.

Referring now to FIG. 3, a balloon-tip catheter 22 having a balloon 24 thereon is percutaneously inserted into blood vessel 11 via the right axillary artery (not shown). This step may be accomplished using standard catherization techniques. The distal end of catheter 22 is then advanced into aorta 16 until balloon 24 is positioned distal to renal arteries 20 as shown in FIG. 3. Balloon 24 is then inflated to and maintained at a size such that fluid communication is substantially terminated in aorta 16 between the portion of blood vessel 11 proximal to balloon 24 and the portion of blood vessel 11 distal to balloon 24. Since conventional balloon-tip catheters may not have a balloon thereon that possess the characteristics necessary to terminate fluid communication in the aorta as described above, modification may be readily made to an existing design of a conventional balloon-tip catheter to achieve the above desired results. One such modification would include providing a balloon on the catheter which is inflatable to an outer diameter which is larger than the inner diameter of the aorta. Another such modification would include providing a coarse textured outer surface to the balloon of the catheter. The above modification would provide increased frictional resistance between the inflated balloon and the sidewall of the blood vessel when force is applied to the balloon in the axial direction thereof. A balloon-tip catheter having a conventional design is available through Medi-tech, Incorporated of Watertown, Mass., as Order No. 17-207 (Description: OBW/40/8/2/100).

Figure 4:
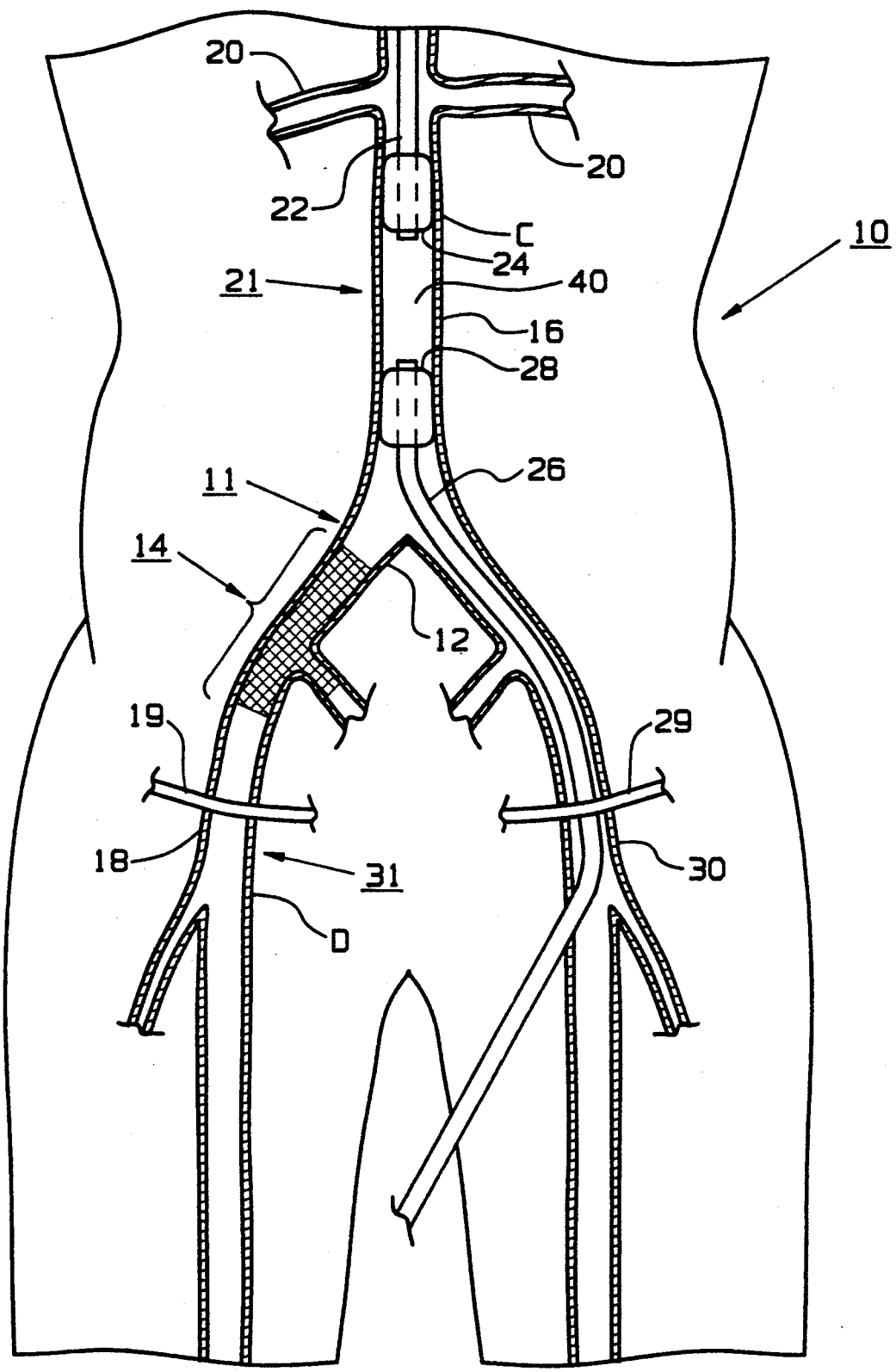
FIG. 4 is a view similar to FIG. 3 but showing a second balloon-tip catheter positioned within the blood vessel wherein the second balloon is inflated in accordance with the preferred method of the present invention.

Referring now to FIG. 4, a balloon-tip catheter 26 having a balloon 28 thereon and an open central lumen defined therein is percutaneously inserted into blood vessel 11 via the left common femoral artery 30. This step may be accomplished using standard catherization techniques. The distal end of catheter 26 is then advanced into aorta 16 until balloon 28 is positioned proximal to the aortic bifurcation. Balloon 28 is then inflated to and maintained at a size such that fluid communication is substantially terminated in aorta 16 between the portion of blood vessel 11 proximal to balloon 28 and the portion of blood vessel 11 distal to balloon 28. Since conventional balloon-tip catheters may not have a balloon thereon that possess the characteristics necessary to terminate fluid communication in the aorta as described above, modification similar to that described with respect to catheter 22 may be need to be made to catheter 26. In addition, further modification may need to be made to catheter 26 since a conventional balloon-tip catheter may not have an open central lumen defined therein which possesses a diameter large enough for the advancement therethrough of a compressed stent mounted on a balloon of another balloon-tip catheter as will be required by the preferred method of the present invention (see FIG. 17). Such further modification would be to create an open central lumen in catheter 26 that possesses a diameter larger than the outer diameter of the compressed stent which is mounted on the balloon of the balloon-tip catheter as referred to above. Due to the increased size requirements of catheter 26 as alluded to above, a surgical cut-down may need to be performed in order to expose left common femoral artery 30. Such exposure would facilitate both placement of catheter 26 into blood vessel 11 and repair of such blood vessel following subsequent removal of such catheter therefrom.

Temporary occlusion of the blood flow in the inferior mesenteric artery (not shown) by laparoscopic procedures may need to be performed in order to prevent the flow of blood from the inferior mesenteric artery into aorta 16 due to placement of inflated balloons 24 and 28 as discussed above.

The region bound by balloon 24 of catheter 22 and balloon 28 of catheter 26 and the sidewall of blood vessel 11 contained therebetween defines a region 40 of the area within blood vessel 11, located near site 21 upstream of occluded segment 14, which is substantially isolated from fluid communication with the rest of the area within blood vessel 11.

Another step according to the method of the present invention comprises making an arteriotomy in the sidewall of blood vessel 11, near upstream site 21, to create a communicating aperture between upstream isolated region 40 and the outside of blood vessel 11.

Figure 5:
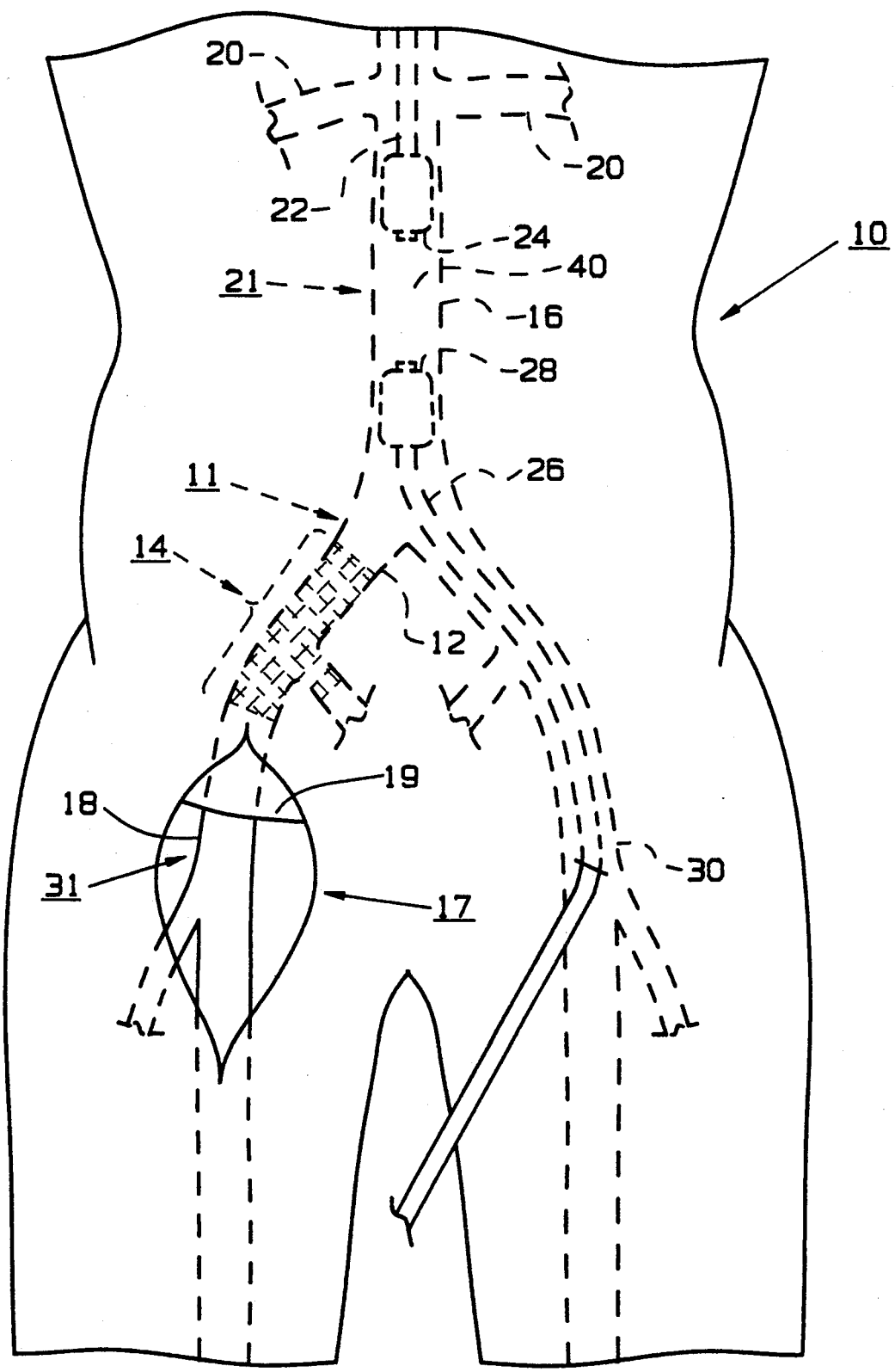
FIG. 5 is a view similar to FIG. 4 but showing the blood vessel in phantom except for a portion thereof that is exposed through a gaping surgical incision. Also shown exposed through the surgical incision in FIG. 5 is a portion of the right inguinal ligament.

Referring now to FIG. 5, right common femoral artery 18 and right inguinal ligament 19 are exposed via a surgical incision 17. Such exposure is accomplished using standard surgical techniques.

Figure 6:
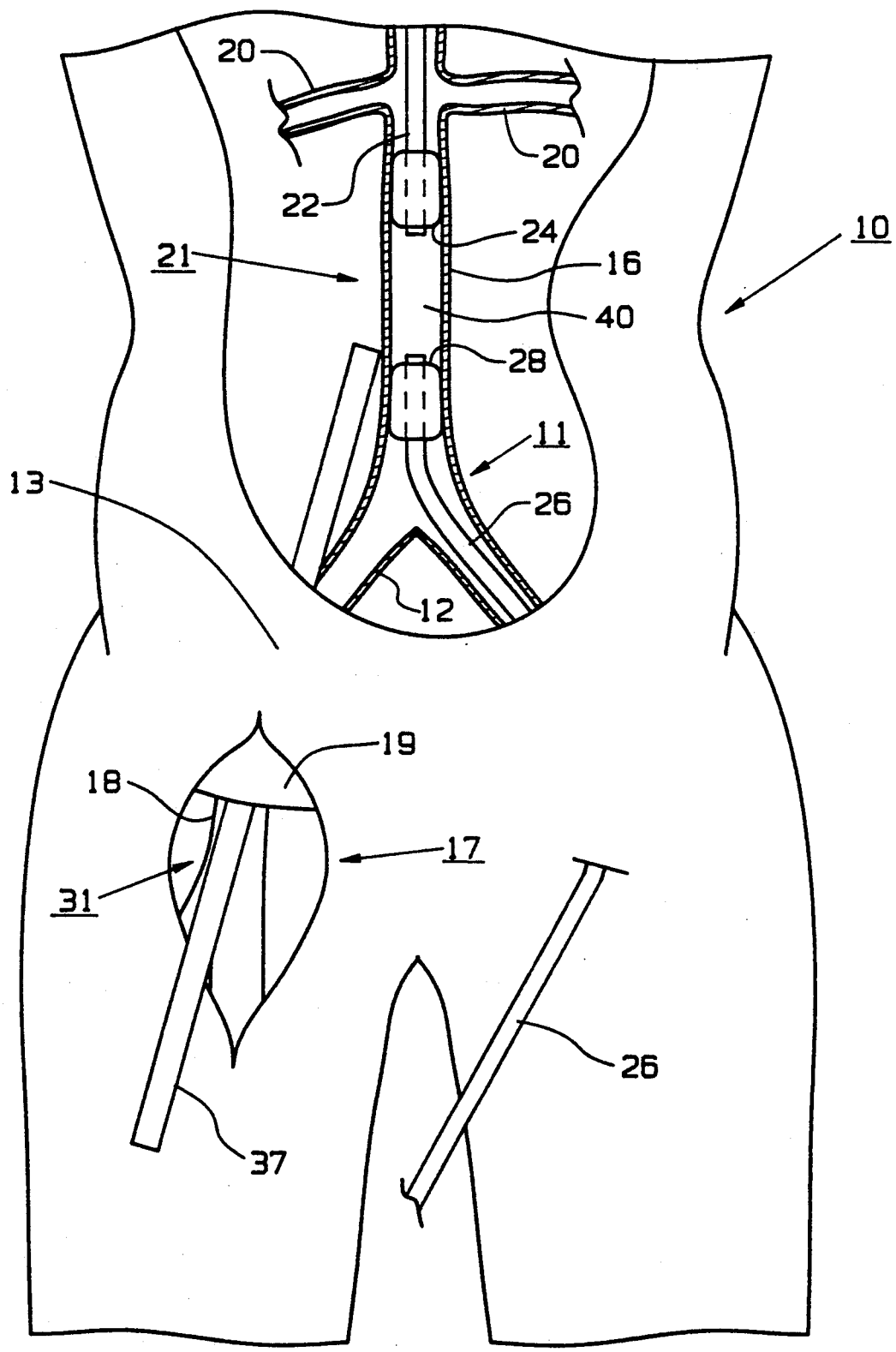
FIG. 6 is a view similar to FIG. 5 but showing another portion of the blood vessel, including the aorta, exposed for clarity of description. Moreover, in FIG. 6, a laparoscope (depicted schematically) is shown inserted through the surgical incision in accordance with the preferred method of the present invention.

Insufflation of the peritoneal cavity is then performed using standard techniques associated with laparoscopy. A laparoscope 37 (see FIG. 6), having an open central lumen (i.e. a working channel) defined therein, is then inserted into human body 10 through the opening between right common femoral artery 18 and right inguinal ligament 19. Laparoscope 37 may additionally include a fiber optic illumination device and a telescope for viewing. A tilt table may be used with the patient (i.e. human body 10) positioned thereon in order to maneuver the patient's abdominal contents away from the laparoscope insertion site and the area near upstream site 21. Laparoscope 37 is then advanced toward upstream site 21 until its distal end is positioned thereat as shown in FIG. 6. One or more additional laparoscopes and associated laparoscopic operating instruments may be employed using standard laparoscopic techniques to assist in the above positioning via direct visualization, tissue retraction and tissue dissection. One laparoscope which may be used in carrying out the preferred mehthod of the present invention is available through Karl Storz Endoscopy-America, Incoporated of Culver City, Calif., as Catalog No. 26075A. Modification may be readily made to laparoscope 37, such as rounding the distal edge thereof, in order to reduce the possibility of tissue trama as a result of advancement of laparoscope 37 within human body 10. A book which discloses various standard laparoscopic techniques and standard associated laparoscopic operating instruments is entitled "Laparoscopy for Surgeons," authored by Barry A. Salky, M.D., published by Igaku-Shoin Medical Publishers, Inc. of New York, N.Y., U.S.A. (1990), and the pertinent part of the disclosure of which is herein incorporated by reference.

Figure 7:
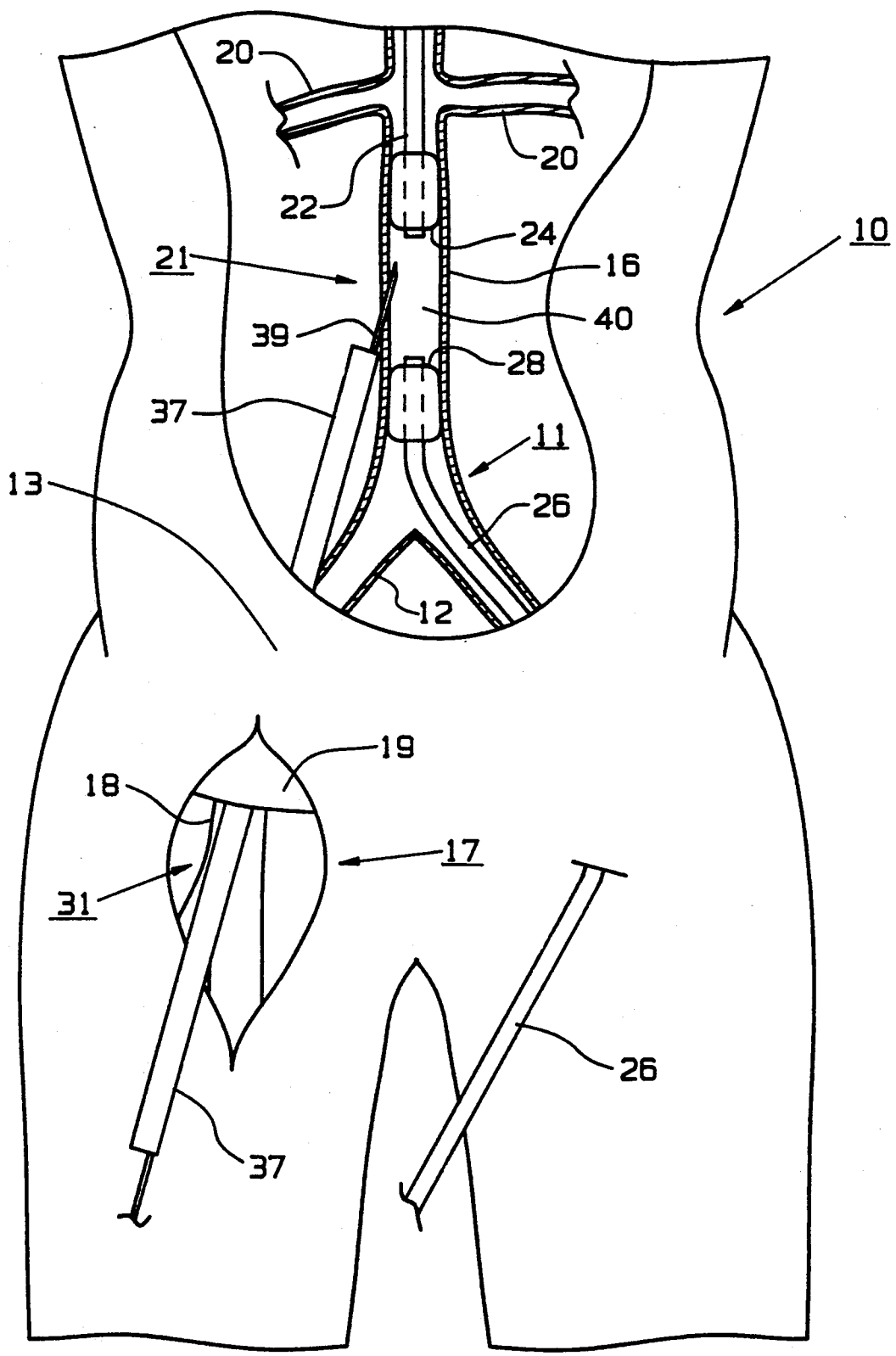
FIG. 7 is a view similar to FIG. 6 but showing a needle positioned within the laparoscope in accordance with the preferred method of the present invention.
Figure 8:
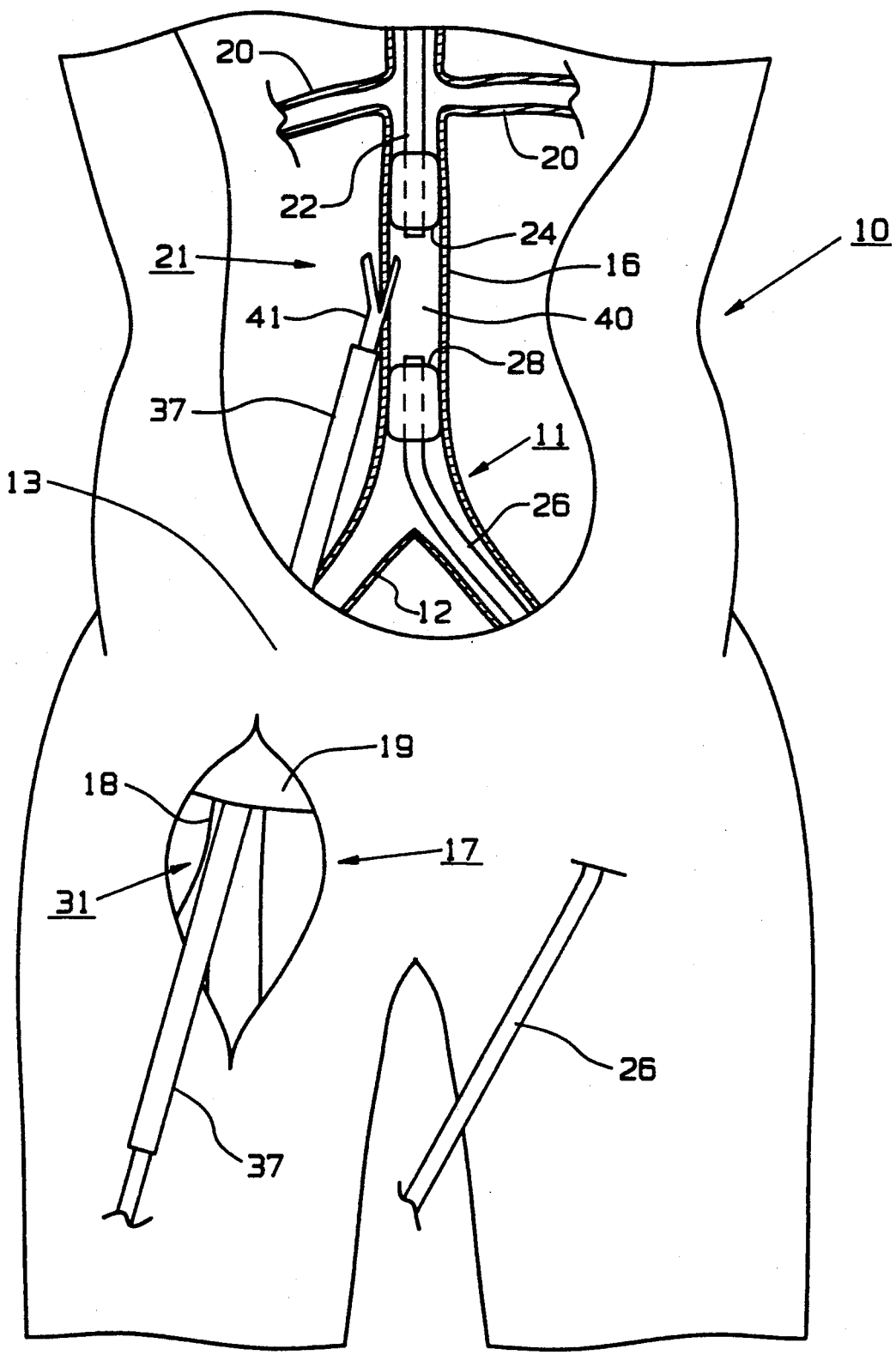
FIG. 8 is a view similar to FIG. 7 but showing the needle removed from the laparoscope and replaced with a scissors device in accordance with the preferred method of the present invention.

Referring now to FIG. 7, a puncture needle 39 is advanced through the open central lumen of laparoscope 37 until its distal end exits the laparoscope. Thereafter, needle 39 is manipulated to penetrate through the sidewall of blood vessel 11 to the inside thereof, thus creating a puncture in the vessel. Needle 39 is then withdrawn and a scissors device 41 is advanced through the open central lumen of laparoscope 37 until its distal end exits the laparoscope (see FIG. 8). The scissors device is then manipulated to enlarge the puncture in the sidewall of the vessel. Scissors device 41 is then withdrawn from laparoscope 37. One puncture needle which may be used in carrying out the preferred method of the present invention is available through Karl Storz Endoscopy-America, Incorporated of Culver City, Calif., as Catalog No. 26178R. Additionally, one scissors device which may be used in carrying out the method of the present invention is available through Karl Storz Endoscopy-America, Incorporated of Culver City, Calif., as Catalog No. 26178PS.

It should be noted that if upstream isolated region 40 was not substantially isolated from fluid communication with the rest of the area within the blood vessel, the act of making an arteriotomy in the sidewall of blood vessel 11 near upstream site 21 would cause significant blood leakage out of blood vessel 11 and such blood leakage may be fatal to the patient.

According to another step of the method of the present invention, a graft prosthesis is positioned so that one end of the graft is located substantially adjacent blood vessel 11 at upstream site 21 and the other end of the graft prosthesis is located substantially adjacent blood vessel 11 at downstream site 31. The above positioning step includes the step of advancing the graft prosthesis within human body 10 with a medical instrument.

Figure 9A:
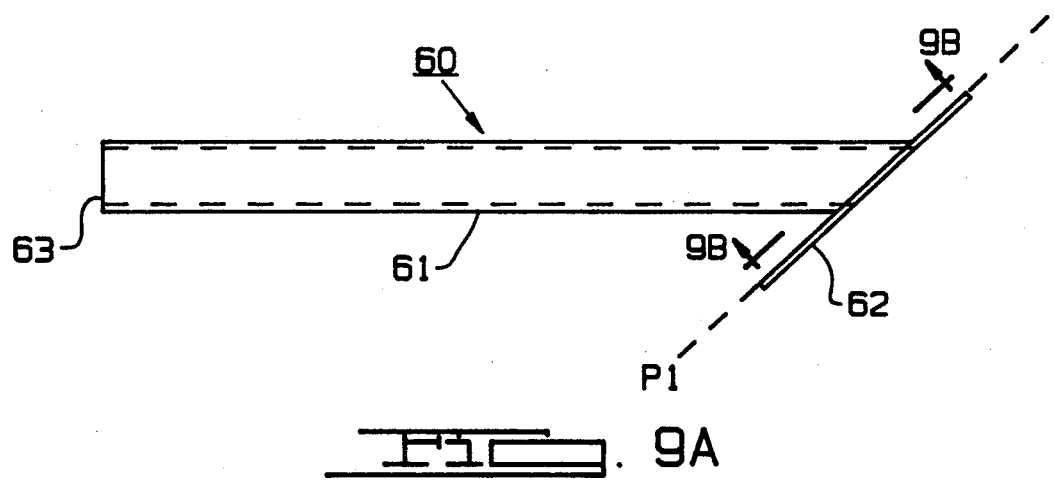
FIG. 9A is an elevational view of a graft prosthesis used in carrying out the preferred method of the present invention.
Figure 9B:
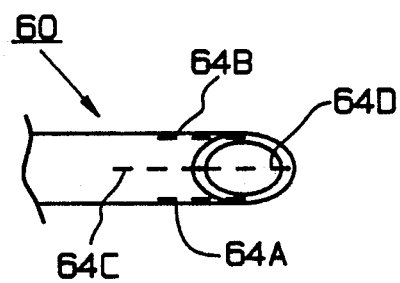
FIG. 9B is a fragmentary sectional view taken along the line 9B—9B of FIG. 9A as viewed in the direction of the arrows.
Figure 9C:
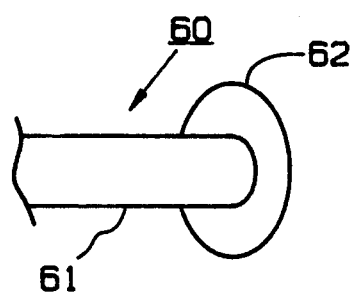
FIG. 9C is a fragmentary perspective view of the graft prosthesis of FIG. 9A showing its outwardly extending flanged end portion.
Figure 9D:
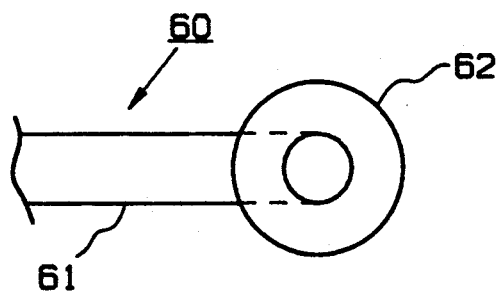
FIG. 9D is another fragmentary perspective view of the graft prosthesis of FIG. 9A showing its outwardly extending flanged end portion.
Figure 9E:
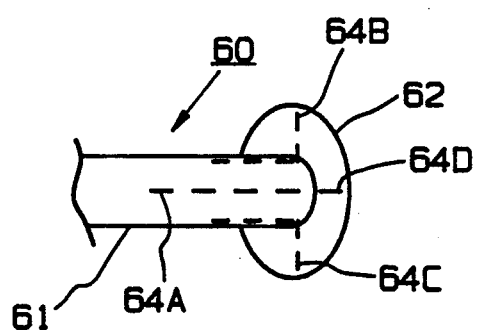
FIG. 9E is a view similar to FIG. 9C but showing a plurality of springs, in phantom, integrally positioned within the outwardly extending flanged end portion, in addition to, a portion of the sidewalls of the graft prosthesis of FIG. 9A.
Figure 9F:
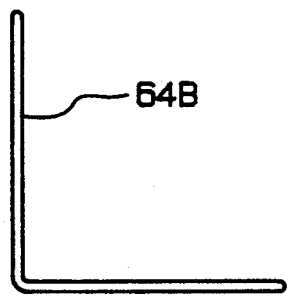
FIG. 9F is an elevational view of one of the plurality of springs of FIG. 9E.
Figure 9G:
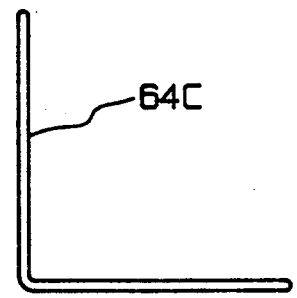
FIG. 9G is an elevational view of another of the plurality of springs of FIG. 9E.
Figure 9H:
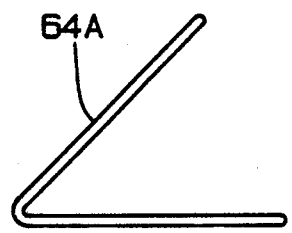
FIG. 9H is an elevational view of yet another of the plurality of springs of FIG. 9E.
Figure 9I:
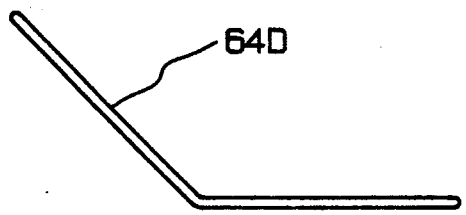
FIG. 9I is an elevational view of still another of the plurality of springs of FIG. 9E.

One type of graft prosthesis which may be used is a graft, generally designated by the reference numeral 60 and shown in FIGS. 9A-9E. Graft 60 includes a body portion 61 having a length slightly larger than the distance between upstream site 21 and downstream site 31. Graft 60 has an outwardly extending flanged end portion 62 as shown in FIGS. 9A, 9C, 9D and 9E. End portion 62 is resiliently maintained outwardly extending by four springs 64A-64D as shown in FIGS. 9B and 9E-9I. In their relaxed state, springs 64A-64D maintain end portion 62 within a plane P1 as shown in FIG. 9A. It should be noted that a number of springs other than four may be used, if desired, to maintain end portion 62 outwardly extending as previously shown and described. Graft 60 further includes a second end portion 63 having a design similar to that of a conventional prosthetic graft as shown in FIGS. 9A. Graft 60 is preferably made of synthetic fibers. By way of example, graft 60 can be made from the material sold under the trademark Dacron by E. I. du Pont de Nemours & Co., Inc of Wilmington, Del. Body portion 61 and end portion 62 of graft 60 are integrally formed together with springs 64A-64D maintained integrally within end portion 62 and a portion of the sidewalls of body portion 61 as shown in FIGS. 9B and 9E. Graft 60 maintains its shape as shown in FIGS. 9A-9E absent application of external forces thereto and also graft 60 will revert back to such shape upon termination of such external forces thereto.

Figure 10A:
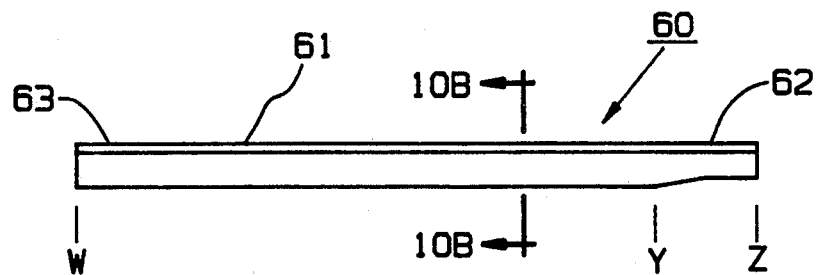
FIG. 10A is an elevational view of the graft prosthesis of FIG. 9A wherein the graft prothesis is in a rolled configuration.
Figure 10B:
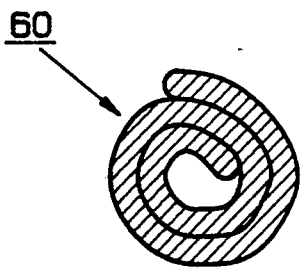
FIG. 10B is a cross-sectional view taken along the line 10B—10B of FIG. 10A as viewed in the direction of the arrows.
Figure 11B:
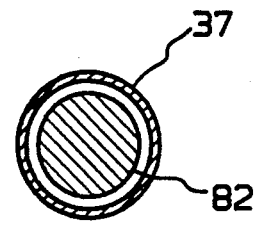
FIG. 11B is a cross-sectional view taken along the line 11B—11B of FIG. 11A as viewed in the direction of the arrows.
Figure 12:
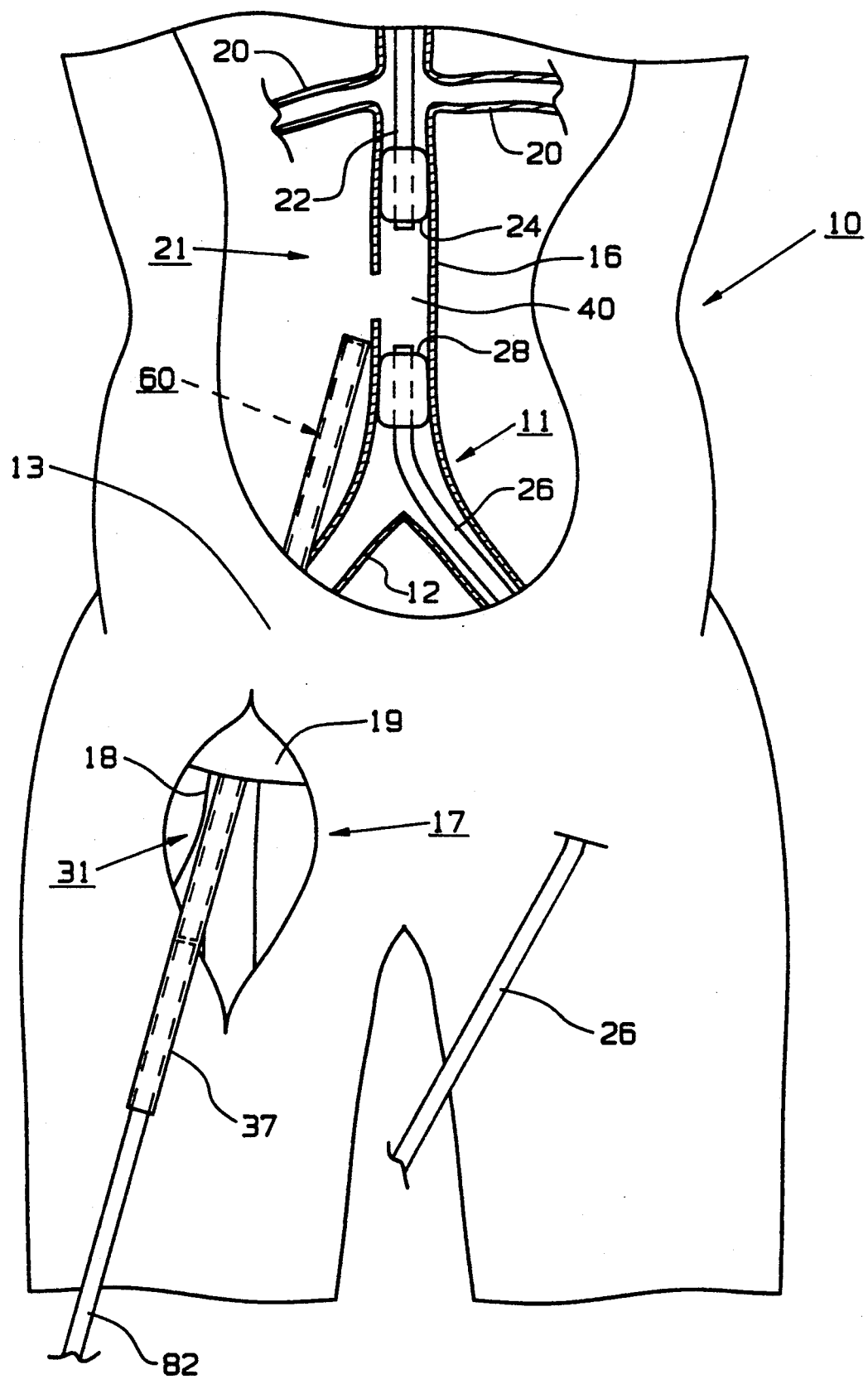
FIG. 12 is a view similar to FIG. 8 but showing the scissors device removed from the laparoscope and replaced with the graft prosthesis and plunger of FIG. 11A in accordance with the preferred method of the present invention.
Figure 13:
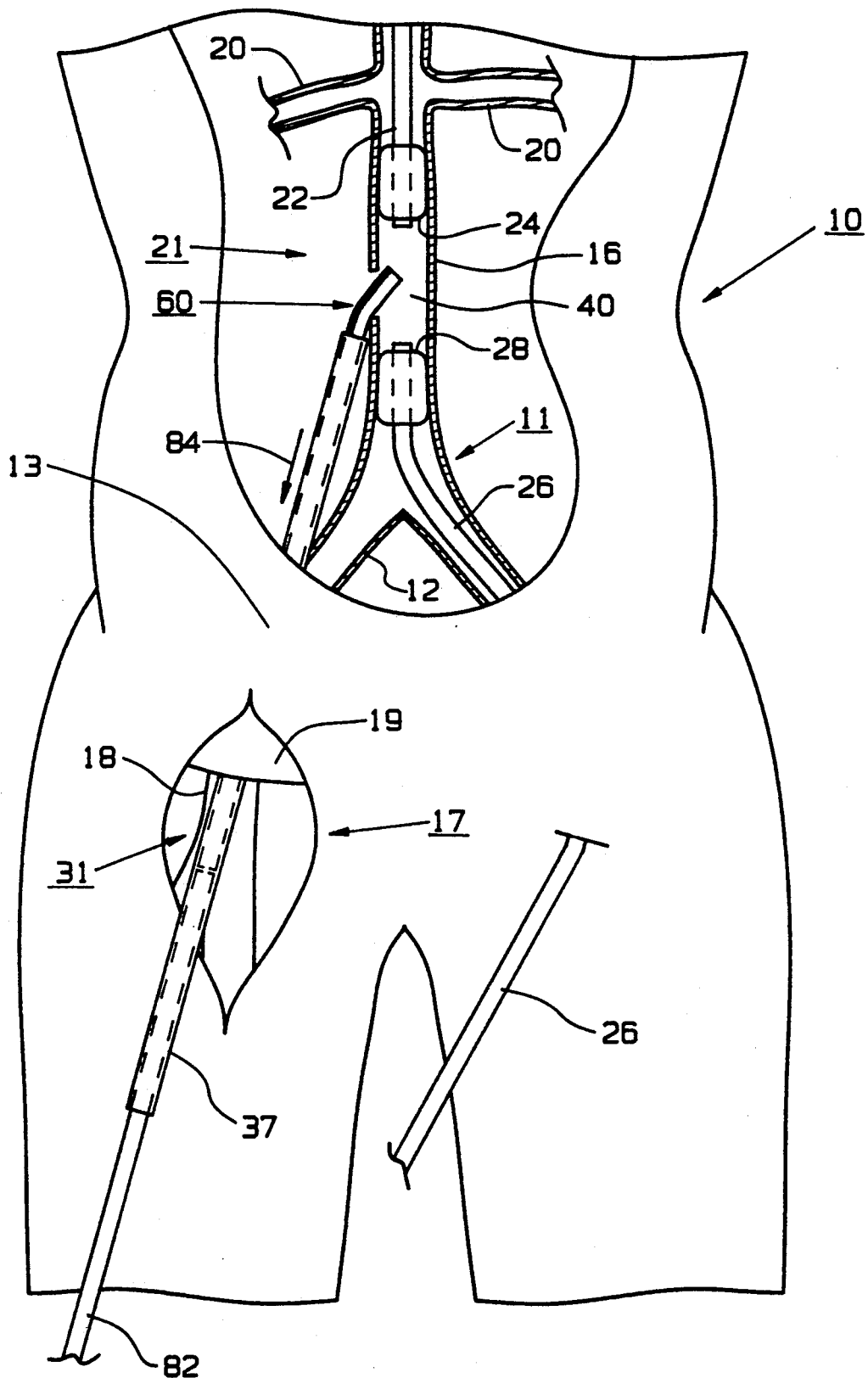
FIG. 13 is a view similar to FIG. 12 but showing the graft prosthesis being advanced out the distal end of the laparoscope in accordance with the preferred method of the present invention.
Figure 14:
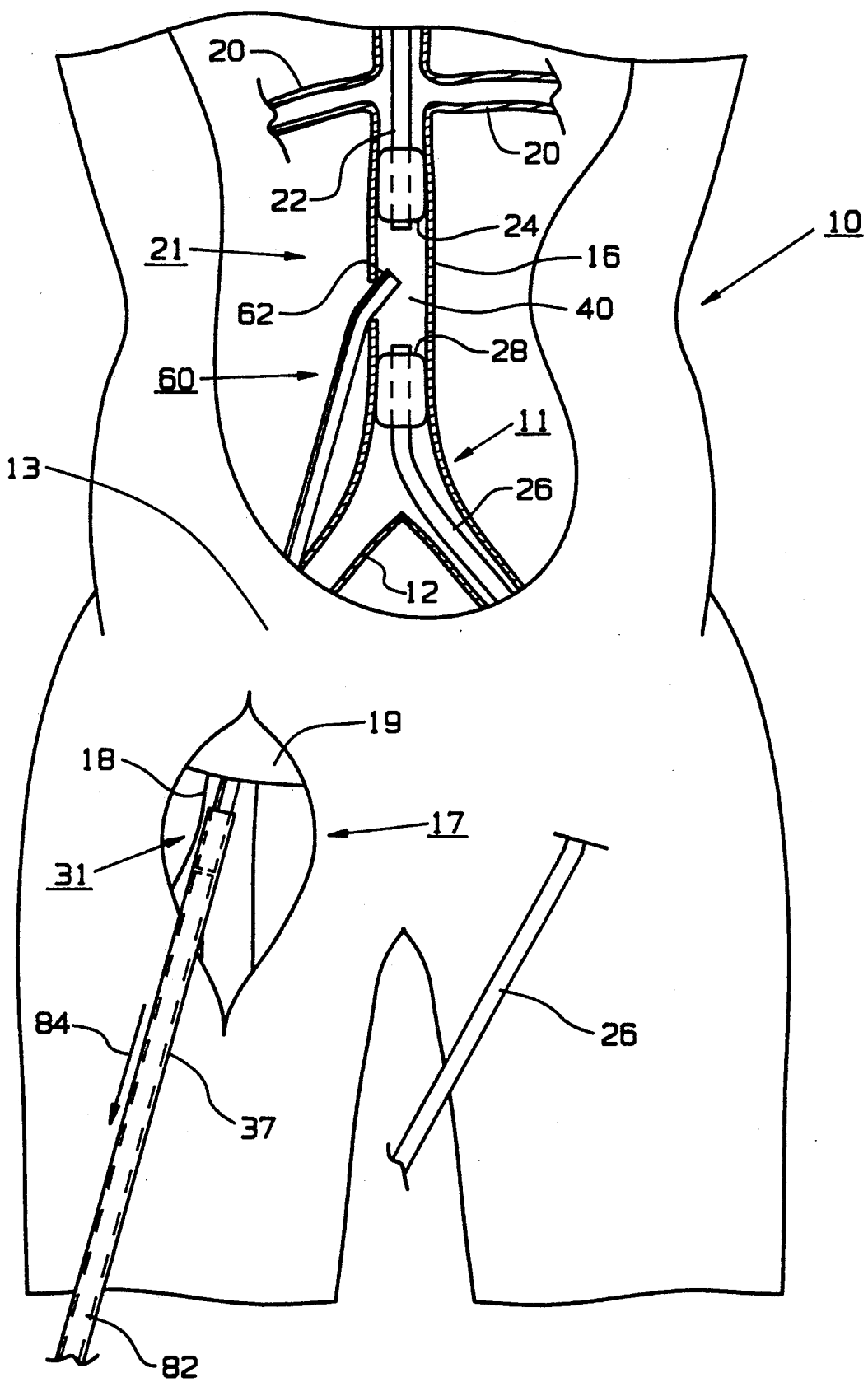
FIG. 14 is a view similar to FIG. 13 but showing the graft prosthesis being further advanced out the distal end of the laparoscope in accordance with the preferred method of the present invention.

Graft 60 is positioned within the open central lumen defined in laparoscope 37. In order to achieve the above, graft 60 is preferably rolled into a substantially cylindrical shape as shown in FIGS. 10A and 10B. End portion 62 of graft 60 is manipulated to lie substantially parallel to body portion 61 of graft 60 while graft 60 is in its rolled configuration as shown in FIG. 10A. The outer diameter of graft 60, in its rolled configuration, from point W to point Y is larger than the outer diameter of the rolled graft from point Y to point Z as shown in FIG. 10A. The above is due to the angular construction of end portion 62 as shown in FIG. 9A. The outer diameter of the rolled graft from point W to point Y is slightly smaller than the inner diameter of laparoscope 37. As a result, in its rolled configuration, graft 60 can be positioned within the open central lumen of laparoscope 37. Moreover, graft 60 can be maintained in its rolled configuration while positioned in the central lumen of laparoscope 37 due to the inner diameter thereof. Graft 60 is then inserted into the proximal end of the central lumen of laparoscope 37 and advanced until its full length is entirely therein. A plunger 82 is insertable into the central lumen of laparoscope 37 as shown in FIGS. 11A and 11B. Plunger 82 has a length sufficient to span the length of laparoscope 37. Plunger 82 enables an operator to selectively position graft 60 within body 10. FIGS. 11A and 12 show graft 60 positioned in the distal portion of the central lumen of laparoscope 37 after being advanced by plunger 82.

Figure 15:
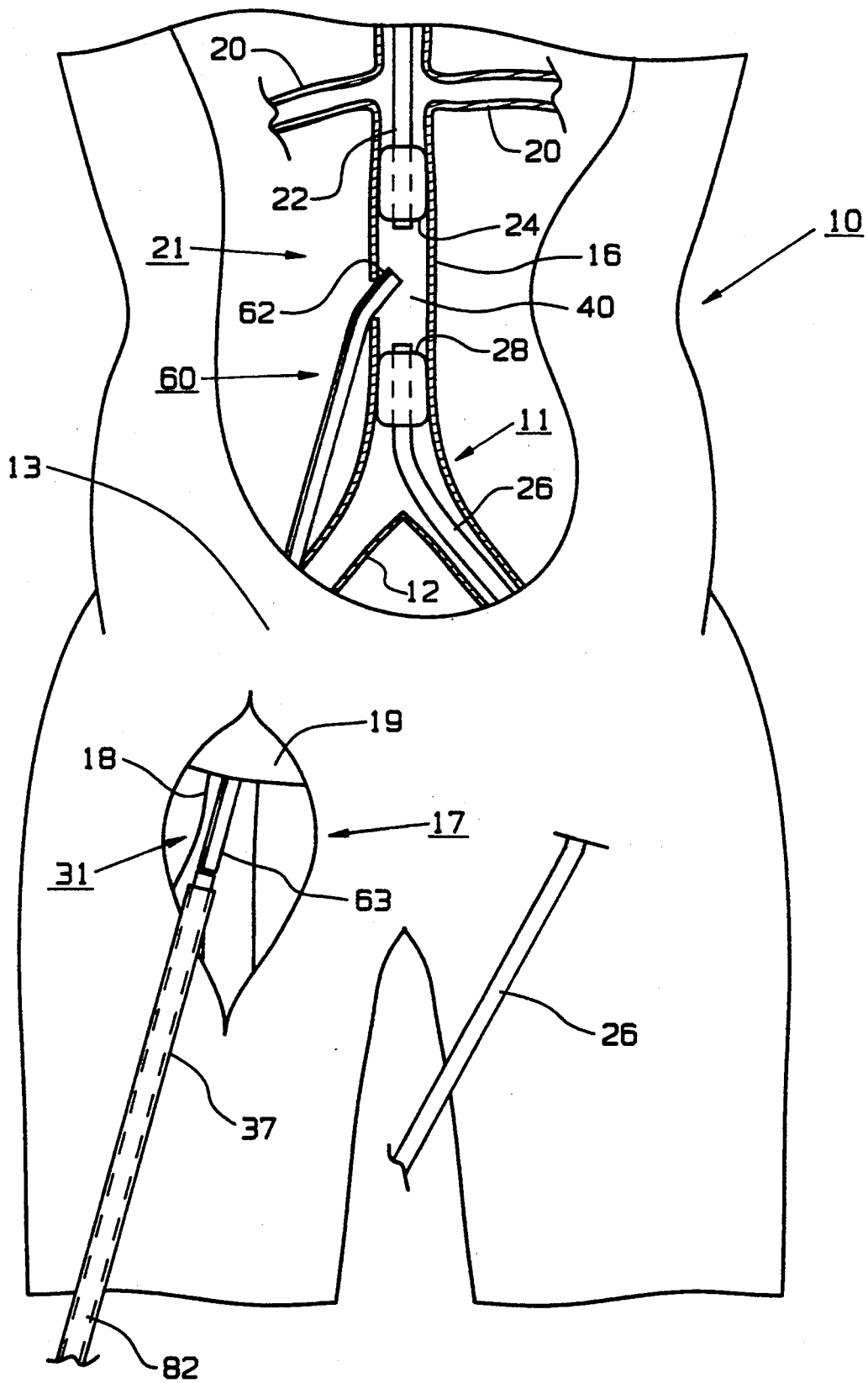
FIG. 15 is a view similar to FIG. 14 but showing the graft prosthesis being yet further advanced out the distal end of the laparoscope in accordance with the preferred method of the present invention.
Figure 16:
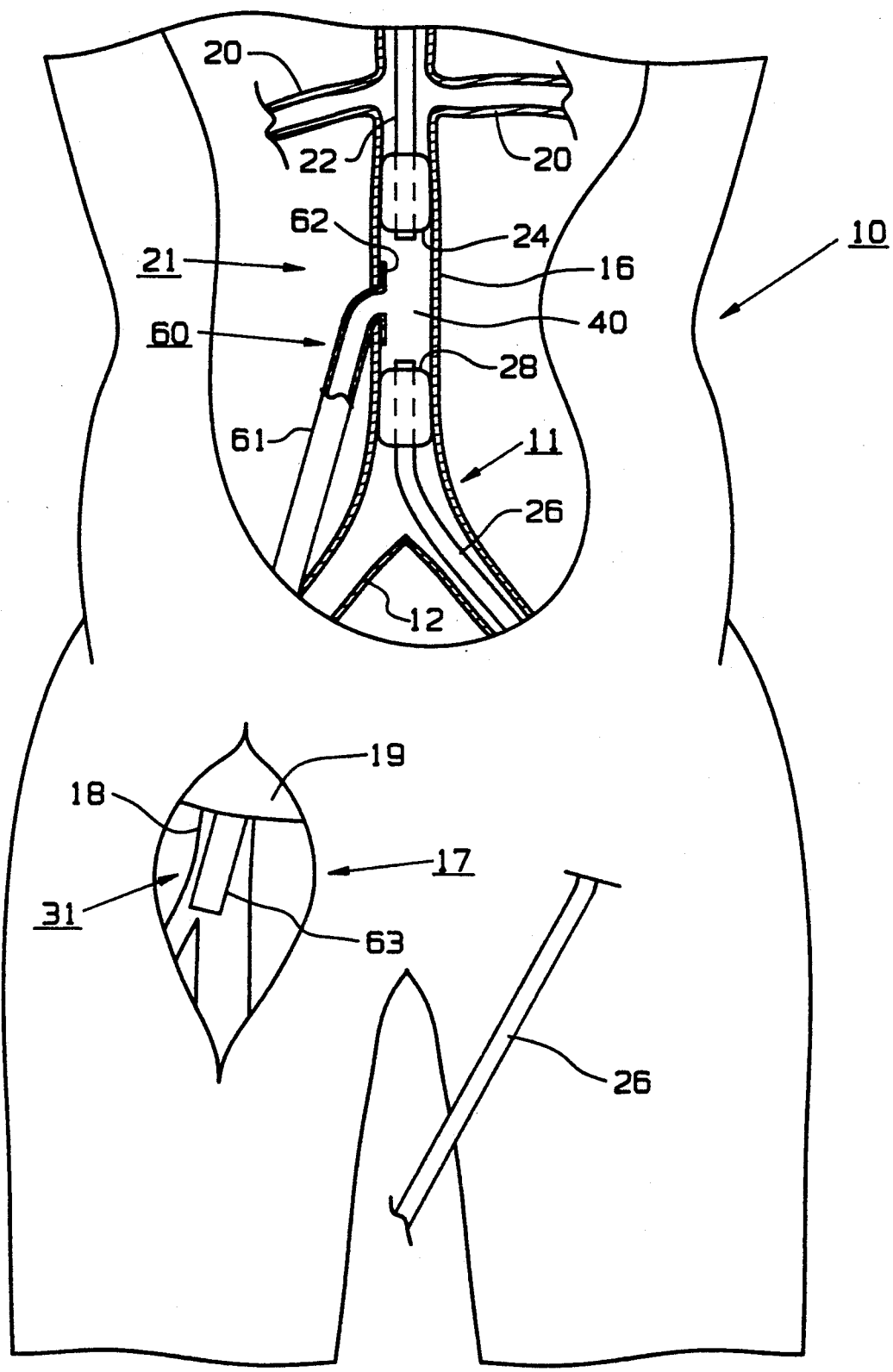
FIG. 16 is a view similar to FIG. 15 but showing the laparoscope removed from the surgical incision and showing the graft prosthesis after it had reverted back to its prerolled configuration in accordance with the preferred method of the present invention.

Laparoscope 37 with graft 60 contained therein is then advanced and manipulated such that the distal end of the laparoscope is advanced through the communicating aperture near upstream site 21 and into upstream isolated region 40. While plunger 82 is held stationary, laparoscope 37 is then withdrawn axially over plunger 82 and graft 60 in the direction of arrow 84 as sequentially shown in FIGS. 13-15. This allows graft 60 in its rolled configuration to be delivered out the distal end of laparoscope 37. FIG. 15 shows end portion 62 of graft 60 positioned within upstream isolated region 40 and end portion 63 of graft 60 positioned at downstream site 31. Since graft 60 is no longer held in its rolled configuration by the inner diameter of the open central lumen of laparoscope 37, graft 60 becomes unrolled and reverts to its prerolled configuration as shown in FIG. 16. Injection of a saline solution into graft 60, via end portion 63, may be performed to facilitate the reverting of graft 60 to its prerolled configuration. Alternatively, an additional laparoscope may be used to manipulate graft 60 to its prerolled configuration. Alternatively, a balloon-tip catheter may be advanced into graft 60 via end portion 63 and the graft converted to its prerolled configuration by inflation and deflation of the balloon along various segments of the graft.

As shown in FIG. 16, end portion 62 of graft 60 is positioned within upstream isolated region 40 near upstream site 21 and end portion 63 of graft 60 is positioned at downstream site 31 while body portion 61 of graft 60 is positioned outside of blood vessel 11. Note that end portion 62 has also reverted back to its prerolled configuration so that such end portion is outwardly extending relative to body portion 61 of graft 60.

Another step according to the preferred method of the present invention comprises forming an anastomosis between end portion 62 of graft 60 and blood vessel 11 near upstream site 21.

Figure 17:
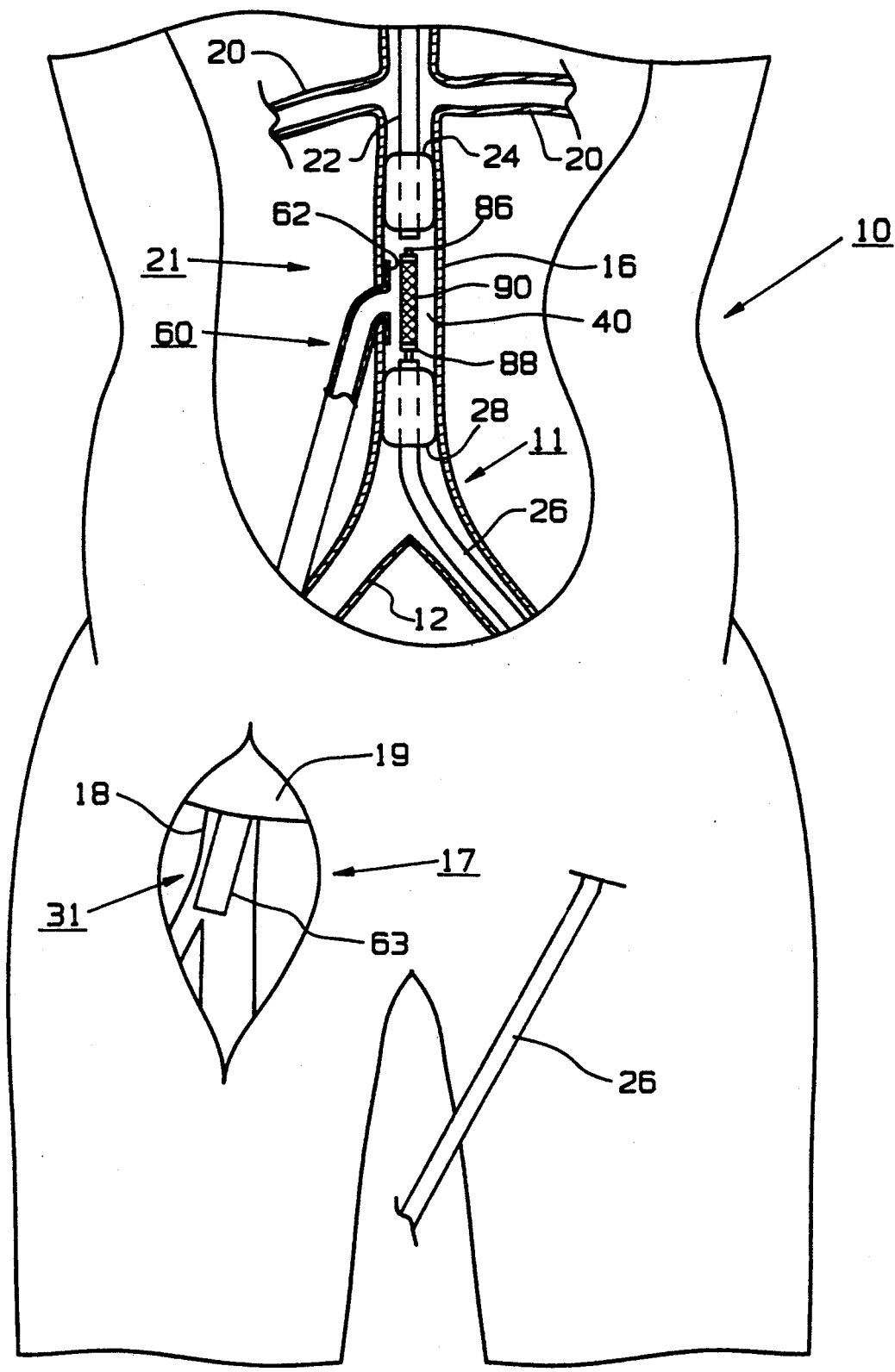
FIG. 17 is a view similar to FIG. 16 but showing a third balloon-tip catheter having a balloon thereon and further having an expandable stent, in its unexpanded state, positioned over the balloon, advanced to a position within the blood vessel in accordance with the preferred method of the present invention.
Figure 18:
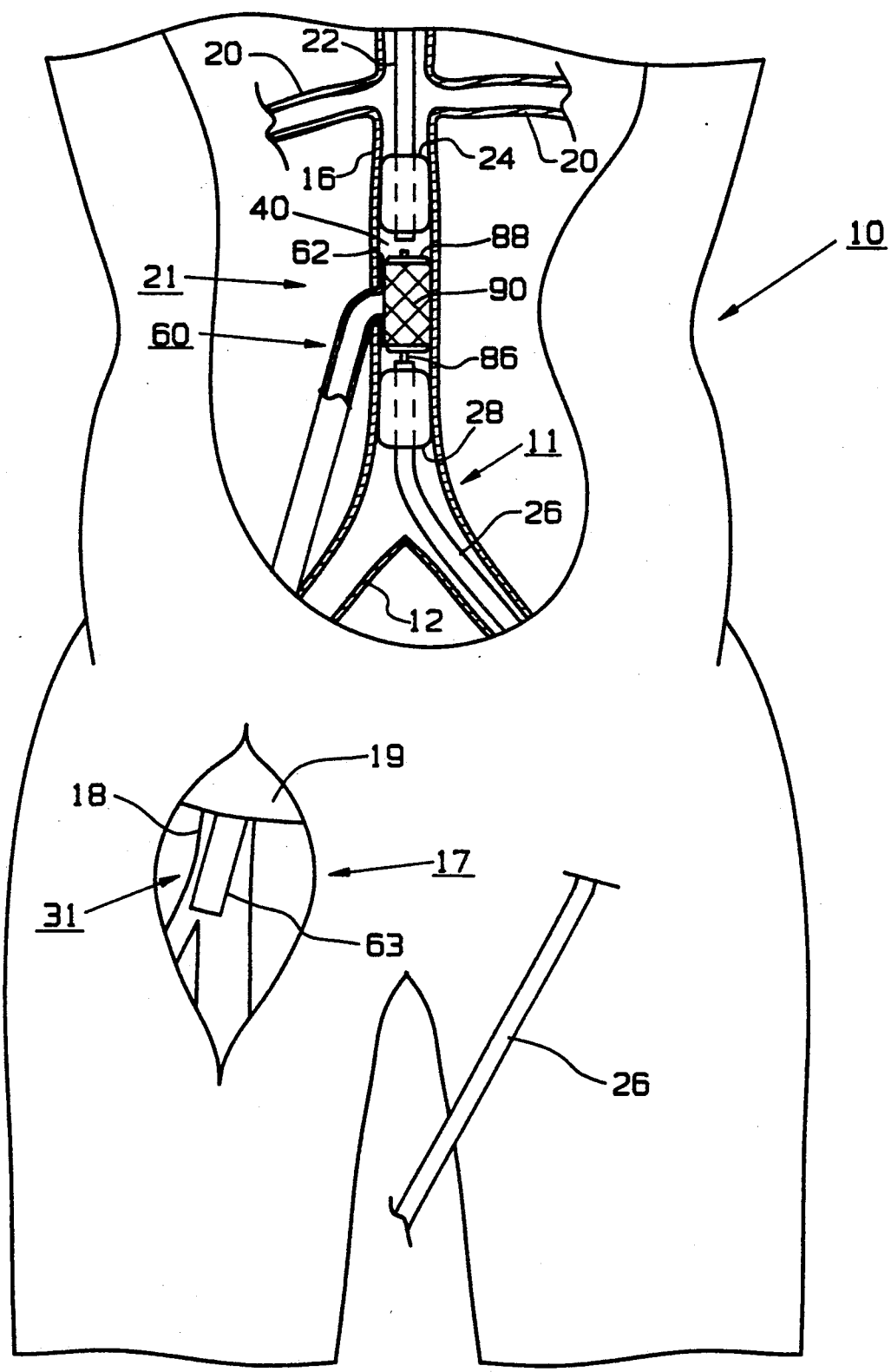
FIG. 18 is a view similar to FIG. 17 but showing the balloon of the third balloon-tip catheter inflated so as to expand the stent into its expanded configuration in accordance with the preferred method of the present invention.
Figure 19:
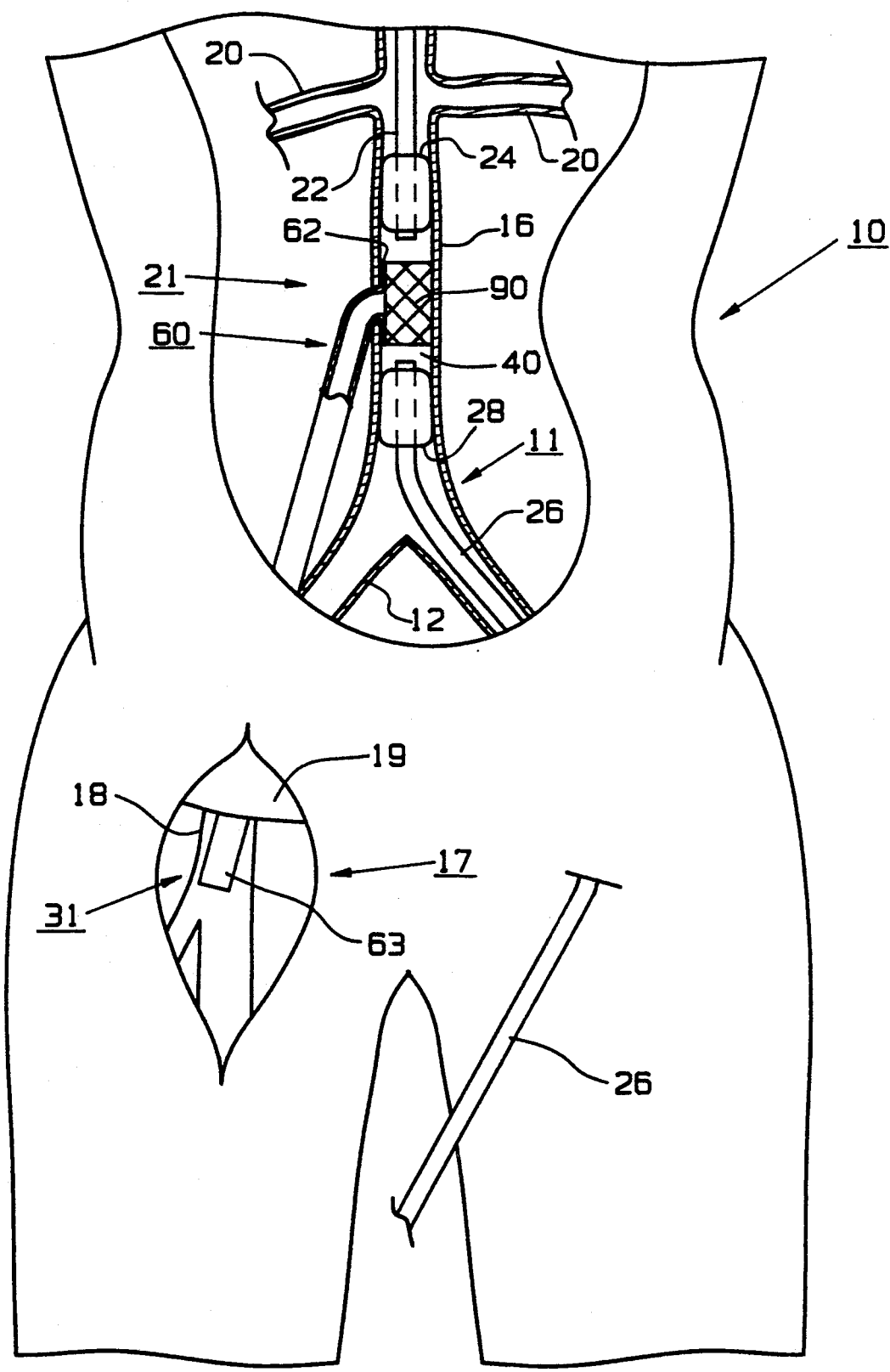
FIG. 19 is a view similar to FIG. 18 but showing the third balloon-tip catheter removed from the blood vessel and showing the stent expanded to form an anastomosis between one end of the graft prosthesis and the blood vessel in accordance with the preferred method of the present invention.

A balloon-tip catheter 86 having a balloon 88 thereon and further having an expandable stent 90, in its unexpanded configuration, positioned over balloon 88 is advanced through the open central lumen of catheter 26 until its distal end is located within upstream isolated region 40 near upstream site 21 (see FIG. 17). Catheter 86 is further advanced until balloon 88 is positioned substantially adjacent end portion 62 of graft 60 as shown in FIG. 17. Balloon 88 is then inflated to expand stent 90 to its expanded configuration such that end portion 62 is secured between stent 90 and the sidewall of blood vessel 11 near upstream site 21 as shown in FIG. 18. Balloon 88 is then deflated and catheter 86 is then removed from body 10 via the central lumen of catheter 26. FIG. 19 shows body 10 after catheter 86 is removed therefrom. Moreover, FIGS. 20A-20C show end portion 62 of graft 60 being forced into the sidewall of blood vessel 11 by stent 90 (in its expanded configuration) such that graft 60 is secured to blood vessel 11 near upstream site 21 at its end portion 62.

One stent which may be used, with a minor degree of modification, in carrying out the preferred method of the present invention is disclosed in U.S. Pat. No. 4,776,337 issued to Palmaz on Oct. 11, 1988, the pertinent part of the disclosure of which is herein incorporated by reference. Such modification would be to provide stent 90 with an outer diameter (in its fully expanded configuration) that is larger than the inner diameter of blood vessel 11 near upstream site 21.

Note that stent 90 includes a plurality of intersecting bars 71 which span the orifice of graft 60 near end portion 62 as shown in FIG. 20B. Intersecting bars 71 which span the above orifice do not substantially hinder blood flow through the graft orifice as demonstrated by the technical article entitled "Intravascular Stents to Prevent Occlusion and Restenosis After Transluminal Angioplasty" which was published in the Mar. 19, 1987 edition of the periodical "The New England Journal of Medicine," the pertinent part of the disclosure of which is herein incorporated by reference.

Further modification may be readily made to stent 90 whereby stent 90 would have an opening defined in its sidewall which is of similar dimensions to the orifice of graft 60 near end portion 62. Such opening would have no intersecting bars traversing thereover. The above modification would allow stent 90 to be positioned within blood vessel 11 near upstream site 21 wherein the above opening would be substantially superimposed over the orifice of graft 60 near end portions 62. This would allow blood to flow through the connection between blood vessel 11 and graft 60 near upstream site 21 in an unimpeded manner.

Figure 21:
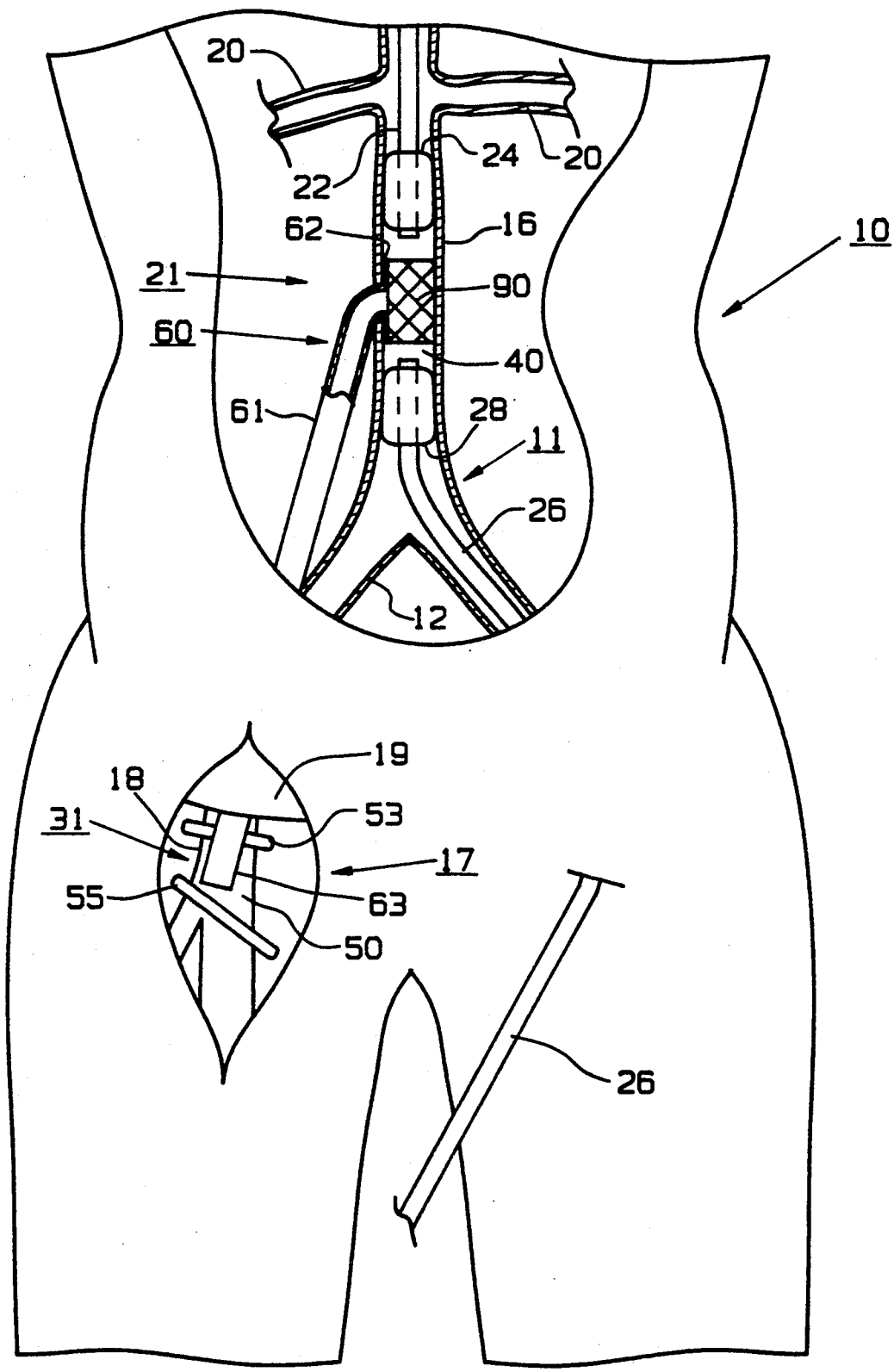
FIG. 21 is a view similar to FIG. 19 but showing a pair of clamps positioned on the blood vessel in accordance with the preferred method of the present invention.

The remainder of the preferred method of the present invention is performed using standard surgical techniques. A book which discloses various standard surgical techniques is entitled "Color Atlas of Vascular Surgery," authored by John S. P. Lumley, published by Wolfe Medical Publications Ltd. of Baltimore, Md. (1986), printed by W. S. Cowell, Ltd. of Ipswich, United Kingdom, and the pertinent part of the disclosure of which is herein incorporated by reference. More specifically, another step according to the preferred method of the present invention comprises isolating a region 50 of the area within blood vessel 11, located near site 31 downstream of occluded segment 14, from fluid communication with the rest of the area within the blood vessel. Referring now to FIG. 21, a pair of surgical clamps 53 and 55 are positioned on blood vessel 11, one being placed upstream of isolated region 50 and the other being placed downstream of isolated region 50.

Figure 22:
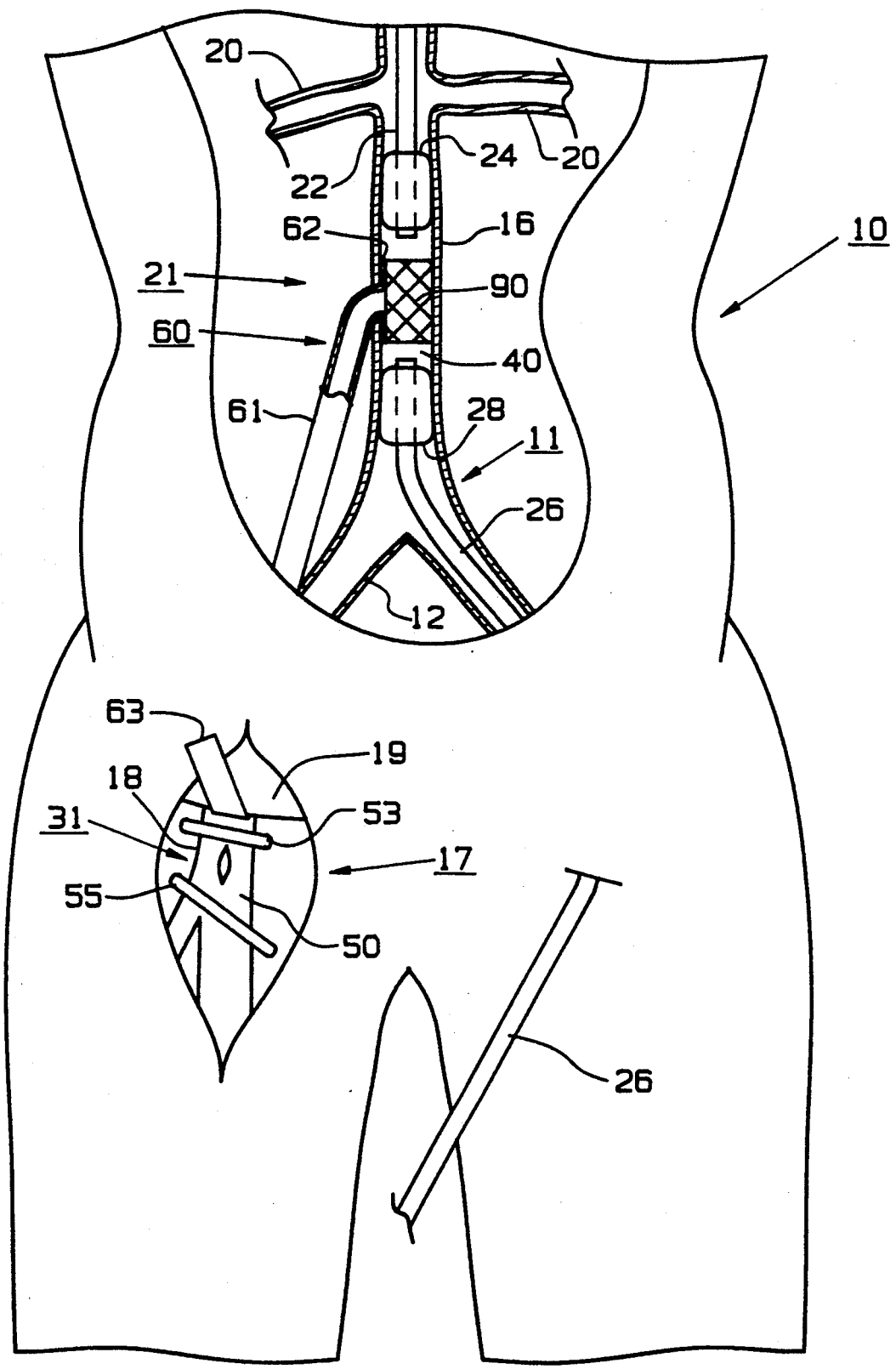
FIG. 22 is a view similar to FIG. 21 but showing an arteriotomy formed in the sidewall of the blood vessel in accordance with the preferred method of the present invention.

Another step according to the method of the present invention comprises making an arteriotomy in the sidewall of blood vessel 11, near downstream site 31, to create a communicating aperture between downstream isolated region 50 and the outside of blood vessel 11. End portion 63 of graft 60 is retracted by surgical forceps (not shown) to expose blood vessel 11 near downstream site 31 (see FIG. 22). A scalpel puncture is then made in blood vessel 11 near downstream site 31 and thereafter the puncture is extended to the appropriate length with a pair of surgical scissors. FIG. 22 shows the communicating aperture defined in the sidewall of blood vessel 11, near downstream site 31.

Figure 23:
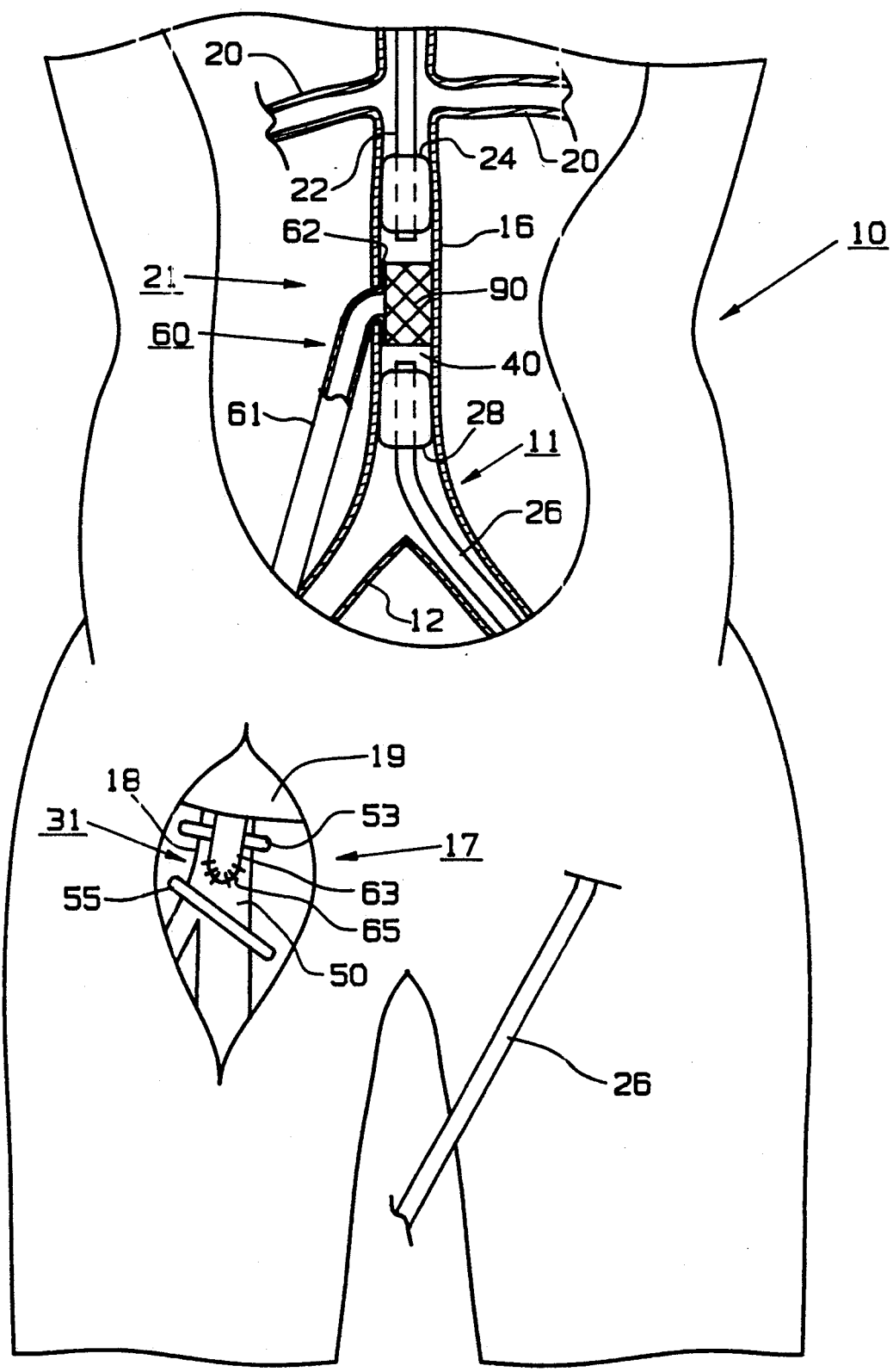
FIG. 23 is a view similar to FIG. 22 but showing an anastomosis formed between the other end of the graft prothesis and the blood vessel in accordance with the preferred method of the present invention.

Another step according to the preferred method of the present invention comprises forming an anastomosis between end portion 63 of graft 60 and blood vessel 11 near downstream site 31. Graft 60 is then cut to an appropriate length and thereafter end portion 63 is cut to an appropriate shape for attachment to blood vessel 11. End portion 63 of graft 60 is then surgically stitched with suture 65 to blood vessel 11 near downstream site 31 as shown in FIG. 23.

Figure 24:
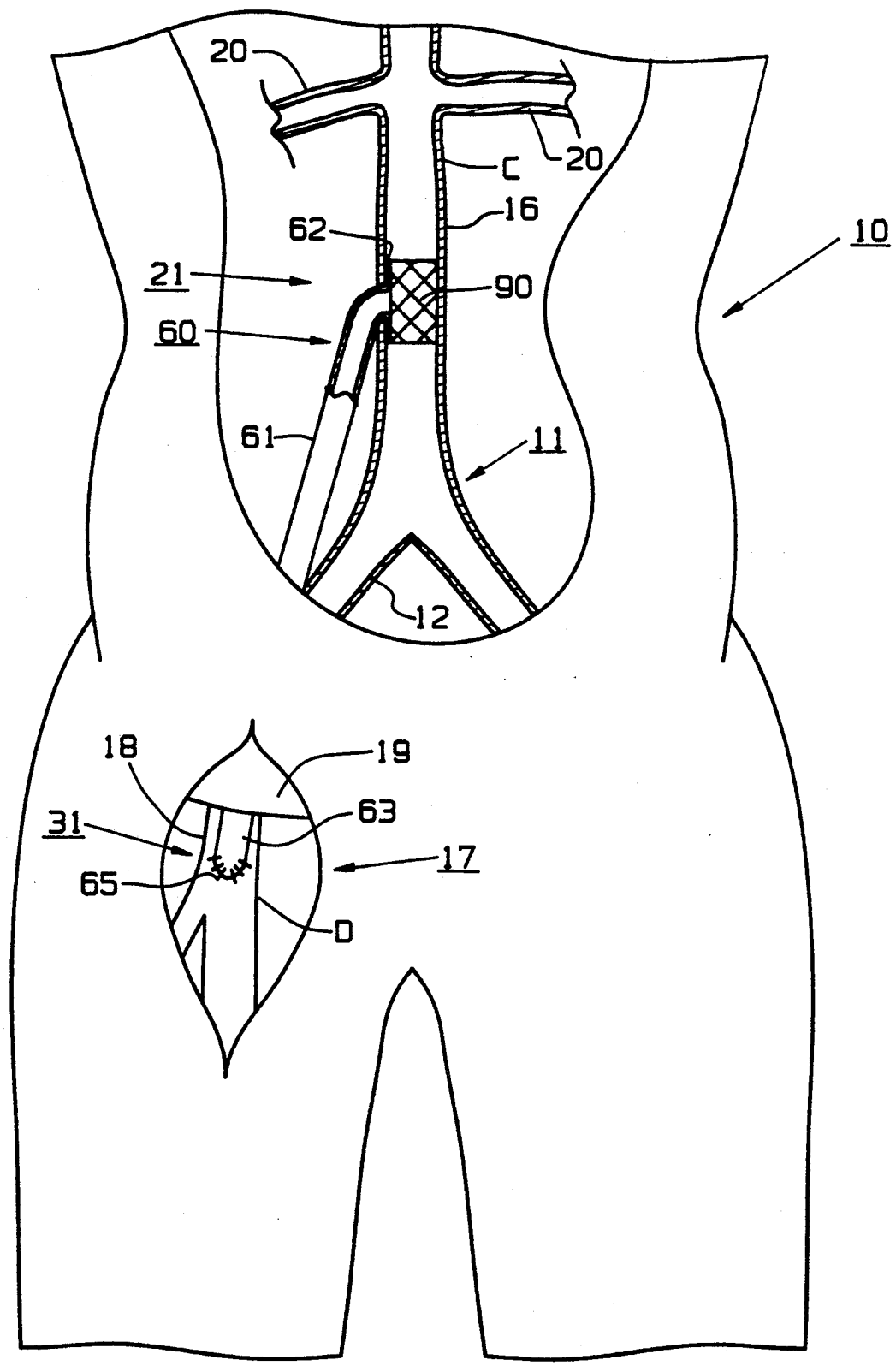
FIG. 24 is a view similar to FIG. 23 but showing the first balloon-tip catheter and the second balloon-tip catheter removed from the blood vessel in accordance with the preferred method of the present invention.

Clamps 53 and 55 are then removed from blood vessel 11, and moreover, balloons 24 and 28 are then deflated and thereafter catheters 22 and 26 are removed from body 10 as shown in FIG. 24. This allows blood to flow to former isolated upstream region 40. Once blood flow reaches former isolated upstream region 40, a flow of blood will enter graft 60 and flow therethrough to former isolated downstream region 50 thereby bypassing occluded segment 14. Consequently, proper blood flow will now exist in body 10 from point C within aorta 16 to point D within right common femoral artery 18 as a result of performing the above described method of bypass of occluded segment 14.

While the invention has been illustrated and described in detail in the drawings and foregoing description, the same is to be considered as illustrative and not restrictive in character, it being understood that only the preferred embodiments and methods have been shown and described and that all changes and modifications that come within the spirit of the invention are desired to be protected.

For instance, it is possible that left common femoral artery 30 and left inguinal ligament 29 could be exposed via a surgical incision similar to that of incision 17 as hereinbefore described. Thereafter, a Y-shaped graft could be utilized instead of graft 60 as hereinbefore disclosed. The Y-shaped graft could be advanced in a rolled configuration through laparoscope 37 and delivered to a position substantially adjacent blood vessel 11 similar in manner to that hereinbefore described. An additional laparoscope could be inserted into human body 10 through the opening defined between left common femoral artery 30 and left inguinal ligament 29 in a manner substantially similar to that hereinbefore described with respect to the insertion of laparoscope 37 into human body 10. The additional laparoscope could be advanced toward the left limb of the Y-shaped graft and thereafter used to grasp such limb and pull it toward left common femoral artery 30 and subsequently out of the surgical incision near the left common femoral artery. The end portion of the left limb of the Y-shaped graft could be cut to an appropriate length and shape, and thereafter, an anastomosis could be made between such end portion and left common femoral artery 30 similar in manner to that hereinbefore described with regard to right common femoral artery 18 and end portion 63 of graft 60.

Moreover, for example, it is possible that a graft may be utilized which would be similar to graft 60 hereinbefore described, however, both end portions of such graft could be similar in structure to end portion 62 of graft 60. In other words, each graft end could posess an end portion that is resiliently maintained outwardly extending relative to the body portion of the graft. A catheter could be placed into blood vessel 11 at right femoral artery 18 and advanced toward occluded segment 14. Prior to arriving at occluded segment 14, the distal end of the catheter could be manipulated and guided out of blood vessel 11 through a puncture site laparoscopically created in the blood vessel in a manner similar to that hereinbefore described. The catheter could then be advanced substantially adjacent blood vessel 11 over and past occluded segment 14. One or more additional laparoscopes could assist in the above advancement. The distal end of the catheter could then be manipulated and guided to reenter blood vessel 11 at a site upstream of occluded segment 14 through a puncture site laparoscopically created in blood vessel 11 in a manner similar to that hereinbefore described. The graft having a resiliently outwardly extending end portion at each end thereof could then be advanced in a rolled configuration through the catheter and delivered to a position substantially adjacent blood vessel 11 similar in manner to that hereinbefore described with respect to graft 60 and laparoscope 37. The graft could have a predetermined length equal to a length slightly larger than the distance between the puncture site located upstream of occluded segment 14 and the puncture site located downstream of occluded segment 14. As a result, the distal end portion of the graft could be positioned within blood vessel 11 at a location upstream of occuluded segment 14 and the proximal end portion of the graft could be positioned within blood vessel 11 at a location downstream of occluded segment 14 while the body portion of the graft could be positioned substantially adjacent and outside of blood vessel 11. Of course, an area within the blood vessel near each end portion of the graft could be isolated from fluid communication with the rest of the area within the blood vessel in a manner substantailly similar to that hereinbefore described with respect to upstream isolated region 40. After being advanced out the distal end of the catheter, the graft (including each outwardly extending end portion) could revert back to its prerolled configuration as hereinbefore described with respect to graft 60. Thereafter, a stent could be placed, in an expanded configuration, adjacent each of the end portions of the graft within blood vessel 11 in order to secure such end portions of the graft to blood vessel 11 as hereinbefore described with respect to stent 90 and end portion 62 of graft 60.

What I claim is:

1. A method of implanting a graft prosthesis in the body of a patient to bypass a segment of a blood vessel comprising the steps of:

making an incision in the body;

positioning a graft so that one end of the graft is located substantially adjacent the blood vessel at a site upstream of the segment and a second end of the graft is located substantially adjacent the blood vessel at a site downstream of the segment, wherein the positioning step includes the step of placing the graft into the body through the incision, and further wherein the positioning step is performed while the upstream site is covered by a substantially intact portion of the epidermis of the body;

isolating a region of the area within the blood vessel near the upstream site from fluid communication with the rest of the area within the blood vessel, wherein the upstream isolating step is performed while the upstream site is covered by the substantially intact portion of the epidermis of the body;

making an arteriotomy in a sidewall of the blood vessel near the upstream site to create a communicating aperture between the upstream isolated region and an area outside of the blood vessel, wherein the upstream arteriotomy making step is performed while the upstream site is covered by the substantially intact portion of the epidermis of the body;

forming an anastomosis between the one end of the graft and the blood vessel near the upstream site, wherein the upstream anastomosis forming step is performed while the upstream site is covered by the substantially intact portion of the epidermis of the body;

isolating a region of the area within the blood vessel near the downstream site from fluid communication with the rest of the area within the blood vessel;

making an arteriotomy in the sidewall of the blood vessel near the downstream site to create a communicating aperture between the downstream isolated region and the area outside of the blood vessel; and forming an anastomosis between the second end of the graft and the blood vessel near the downstream site.

2. The method of claim 1, wherein the positioning step includes the step of advancing the one end of the graft within the body to the upstream site with a medical instrument.

3. The method of claim 2, wherein the medical instrument is a laparoscope.

4. The method of claim 2, wherein the medical instrument has an open lumen defined therein.

5. The method of claim 4, wherein the upstream arteriotomy making step includes the step of advancing a puncture needle within the lumen of the medical instrument.

6. The method of claim 5, wherein the upstream arteriotomy making step further includes the step of penetrating the distal end of the puncture needle through the sidewall of the blood vessel near the upstream site.

7. The method of claim 6, wherein the upstream arteriotomy making step further includes the step of advancing a scissors device within the lumen of the medical instrument.

8. The method of claim 7, wherein the upstream arteriotomy making step further includes the step of cutting the sidewall of the blood vessel near the upstream site with the scissors device.

9. The method of claim 4, wherein the positioning step further includes the step of advancing the graft within the lumen of the medical instrument.

10. The method of claim 9, wherein the positioning step further includes the step of locating the graft within the lumen of the medical instrument in the distal end portion thereof.

11. The method of claim 10, wherein the positioning step further includes the step of forcing the graft out the distal end of the medical instrument.

12. The method of claim 11, wherein the forcing step includes the step of advancing a plunger within the lumen of the medical instrument.

13. The method of claim 12, wherein the forcing step further includes the step of holding the plunger stationary and concurrently advancing the medical instrument axially over the plunger.

14. The method of claim 9, wherein the graft is in a compressed state during advancement thereof within the lumen of the medical instrument.

15. The method of claim 14, wherein the graft is rolled into the compressed state.

16. The method of claim 15, wherein the medical instrument is a laparoscope.

17. The method of claim 1, wherein the graft includes an outwardly extending flanged end portion.

18. The method of claim 17, wherein the upstream anastomosis forming step includes the step of advancing the flanged end portion of the graft into the upstream isolated region.

19. The method of claim 18, wherein the upstream anastomosis forming step further includes the step of advancing a stent within the blood vessel.

20. The method of claim 19, wherein the upstream anastomosis forming step further includes the step of placing the stent substantially adjacent the flanged end portion of the graft.

21. The method of claim 20, wherein the flanged end portion of the graft is interposed between the stent and the sidewall of the blood vessel.

22. The method of claim 21, wherein the flanged end portion of the graft is forced into the sidewall of the blood vessel so as to secure the graft thereto.

23. The method of claim 19, wherein the stent is deformable from an unexpanded configuration to an expanded configuration.

24. The method of claim 23, wherein the upstream anastomosis forming step further includes the step of advancing a ballon-tip catheter within the blood vessel.

25. The method of claim 24, wherein the upstream anastomosis forming step further includes the step of positioning the stent, in the unexpanded configuration, over the balloon of the balloon-tip catheter.

26. The method of claim 25, wherein the upstream anastomosis forming step further includes the step of advancing the balloon and the stent to a position substantially adjacent the flanged end portion of the graft.

27. The method of claim 26, wherein the upstream anastomosis forming step further includes the step of inflating the balloon to expand the stent to the expanded configuration.

28. The method of claim 27, wherein the flanged end portion of the graft is interposed between the stent and the sidewall of the blood vessel.

29. The method of claim 28, wherein the flanged end portion of the graft is forced into the sidewall of the blood vessel so as to secure the graft thereto.

30. The method of claim 1, wherein the upstream isolating step includes the step of advancing a balloon-tip catheter within the blood vessel.

31. The method of claim 30, wherein the upstream isolating step further includes the step of inflating the balloon of the balloon-tip catheter at a location within the blood vessel upstream of the segment.

32. The method of claim 31, wherein the upstream isolating step further includes the step of advancing a second balloon-tip catheter within the blood vessel.

33. The method of claim 32, wherein the upstream isolating step further includes the step of inflating the balloon of the second balloon-tip catheter at a location within the blood vessel upstream of the segment and downstream of the balloon of the first balloon-tip catheter.

34. The method of claim 33, wherein the region bound by the balloon of the first balloon-tip catheter, the balloon of the second balloon-tip catheter and the sidewall of the blood vessel contained therebetween defines the upstream isolated region.

35. The method of claim 2, wherein the step of advancing the one end of the graft includes the step of guiding the one end of the graft beneath another substantially intact portion of the epidermis of the body.

36. The method of claim 35, wherein the guiding step further includes the step of advancing the one end of the graft from a location near the downstream site to a location near the upstream site.

37. The method of claim 1, wherein the upstream anastomosis forming step includes the step of securing the one end of the graft to the blood vessel near the upstream site with an expandable stent.

38. The method of claim 1, wherein the downstream isolating step, the downstream arteriotomy making step and the downstream anastomosis forming step are each performed while a portion of the blood vessel near the downstream site is exposed through the incision.

39. A method for implanting an end portion of a graft within the body of a patient during a bypass grafting procedure, comprising the steps of:

making an incision in the body at a first location;

isolating a region of the area within a blood vessel of the body substantially adjacent a second location from fluid communication with the rest of the area within the blood vessel, wherein the first location is remote from the second location, and further wherein the isolating step is performed while the second location is covered by a substantially intact portion of the epidermis of the body;

making an arteriotomy in a sidewall of the blood vessel substantially adjacent the second location to create a communicating aperture between the isolated region and an area outside of the blood vessel, wherein the arteriotomy making step is performed while the second location is covered by the substantially intact portion of the epidermis of the body;

advancing the end portion of the graft through the incision to the second location which is substantially adjacent the blood vessel, wherein the advancing step is performed while the second location is covered by the substantially intact portion of the epidermis of the body; and forming an anastomosis between the end portion of the graft and the blood vessel substantially adjacent the second location, wherein the anastomosis forming step is performed while the second location is covered by the substantially intact portion of the epidermis of the body.

40. The method of claim 39, wherein the anastomosis forming step includes the step of securing the end portion of the graft to the blood vessel substantially adjacent the second location with an expandable stent.

* * * * *